(12) United States Patent
Kashyap et al.

(10) Patent No.: US 10,806,934 B2
(45) Date of Patent: Oct. 20, 2020

(54) CUSTOMIZED TARGETED FIELDS FOR ELECTROTHERAPY APPLICATIONS

(71) Applicant: Boston Scientific Neuromodulation Corporation, Valencia, CA (US)

(72) Inventors: Dheerendra Raghavendra Kashyap, Valencia, CA (US); Sarvani Grandhe, Valencia, CA (US); Natalie A. Brill, Valencia, CA (US); Bradley Lawrence Hershey, Valencia, CA (US); Changfang Zhu, Valencia, CA (US); Sridhar Kothandaraman, Valencia, CA (US); Dennis Zottola, Ventura, CA (US); Michael A. Moffitt, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 131 days.

(21) Appl. No.: 15/682,965

(22) Filed: Aug. 22, 2017

(65) Prior Publication Data

US 2018/0056078 A1 Mar. 1, 2018

Related U.S. Application Data

(60) Provisional application No. 62/379,730, filed on Aug. 25, 2016.

(51) Int. Cl.
*A61N 1/372* (2006.01)
*A61N 1/36* (2006.01)
(Continued)

(52) U.S. Cl.
CPC ....... *A61N 1/37247* (2013.01); *A61N 1/0551* (2013.01); *A61N 1/36071* (2013.01);
(Continued)

(58) Field of Classification Search
CPC ............ A61N 1/372347; A61N 1/0551; A61N 1/36071
See application file for complete search history.

(56) References Cited

U.S. PATENT DOCUMENTS

| 6,052,624 A | 4/2000 | Mann |
| 8,412,345 B2 | 4/2013 | Moffitt |
(Continued)

FOREIGN PATENT DOCUMENTS

WO WO-2018039166 A1 3/2018

OTHER PUBLICATIONS

"International Application Serial No. PCT/US2017/047908, International Preliminary Report on Patentability dated Mar. 7, 2019", 9 pgs.
(Continued)

*Primary Examiner* — Joseph M Dietrich
(74) *Attorney, Agent, or Firm* — Schwegman Lundberg & Woessner, P.A.

(57) ABSTRACT

A neuromodulation customization system includes a field definition user interface, a neuromodulation signaling engine, and a supervisor engine. The field definition user interface is to facilitate entry of a customized electrotherapy field definition, with the field definition user interface including a set of input controls for defining field shape, field intensity, and field steering parameters of the customized electrotherapy field. The neuromodulation signaling engine is to produce commands for neuromodulation output circuitry to control generation of a customized electrotherapy field via a set of electrodes based on the customized electrotherapy field definition. The supervisor engine is to assess compliance of the customized electrotherapy field to be generated with applicable predefined criteria, and to modify
(Continued)

generation of the customized electrotherapy field in response to an assessed non-compliance with the criteria.

20 Claims, 17 Drawing Sheets

(51) Int. Cl.
  *G16H 40/63* (2018.01)
  *G16H 20/30* (2018.01)
  *A61N 1/05* (2006.01)

(52) U.S. Cl.
  CPC ..... *A61N 1/36142* (2013.01); *A61N 1/36182* (2013.01); *A61N 1/36185* (2013.01); *G16H 20/30* (2018.01); *G16H 40/63* (2018.01); *A61N 1/36062* (2017.08)

(56) References Cited

U.S. PATENT DOCUMENTS

| | | |
|---|---|---|
| 8,812,124 B2 | 8/2014 | Lee |
| 8,868,196 B2 | 10/2014 | Lee et al. |
| 8,909,350 B2 | 12/2014 | Lee |
| 9,044,610 B2 | 6/2015 | Rosenberg et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2011/0093042 A1 | 4/2011 | Torgerson et al. |
| 2015/0217116 A1* | 8/2015 | Parramon .......... A61N 1/36071 607/59 |
| 2016/0001087 A1 | 1/2016 | Moffitt |
| 2016/0030750 A1* | 2/2016 | Bokil ................. A61N 1/36128 607/45 |
| 2016/0074662 A1* | 3/2016 | Moffitt ............... A61N 1/36146 607/72 |
| 2016/0228706 A1* | 8/2016 | Hershey ............. A61N 1/36071 |

OTHER PUBLICATIONS

"International Application Serial No. PCT/US2017/047908, International Search Report dated Nov. 28, 2017", 5 pgs.

"International Application Serial No. PCT/US2017/047908, Written Opinion dated Nov. 28, 2017", 9 pgs.

"European Application Serial No. 17761402.1, Response to Communication Pursuant to Rules 161 & 162 filed Oct. 14, 2019", 16 pgs.

* cited by examiner

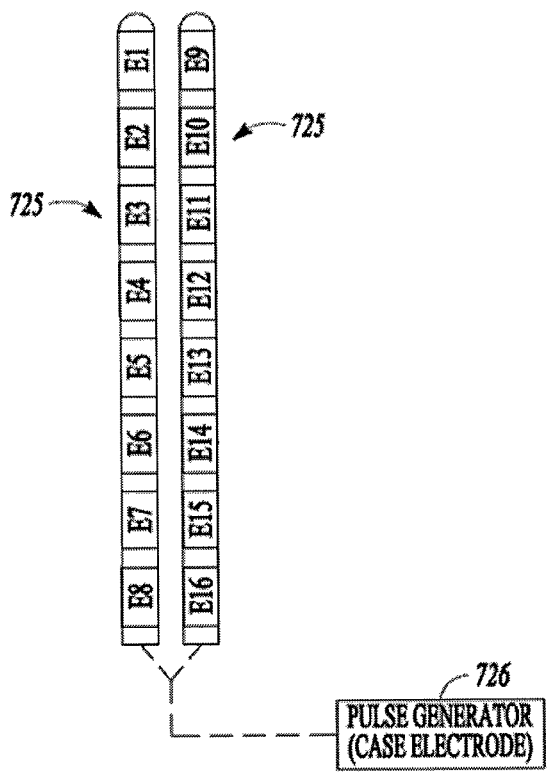
FIG. 7
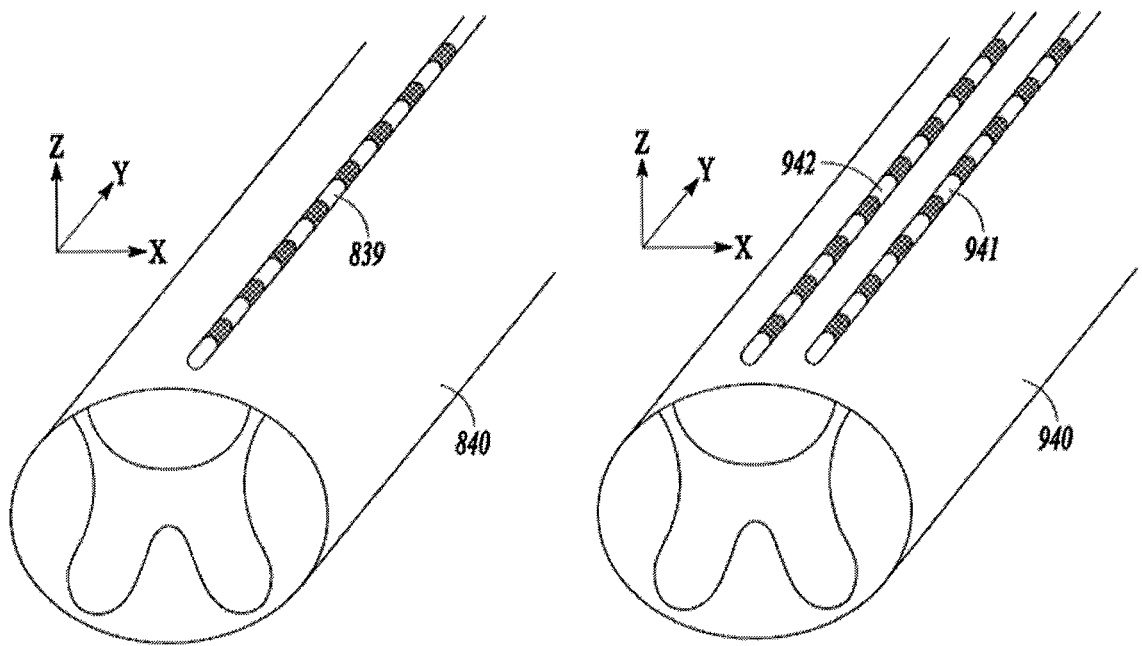
FIG. 8
FIG. 9

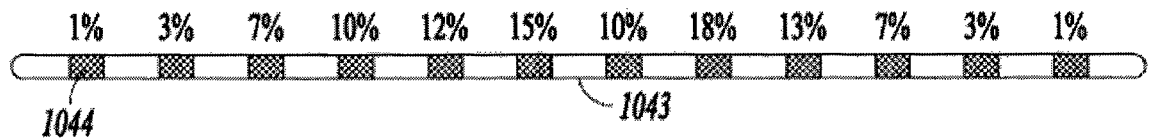
FIG. 10
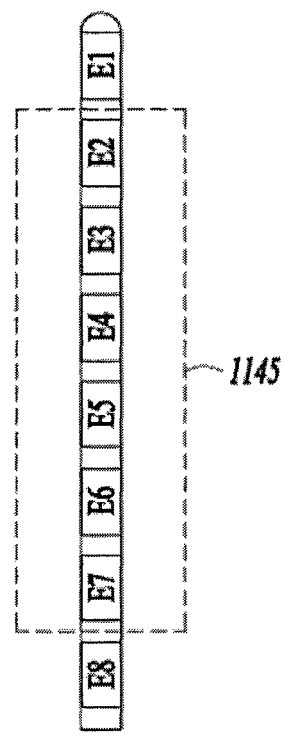
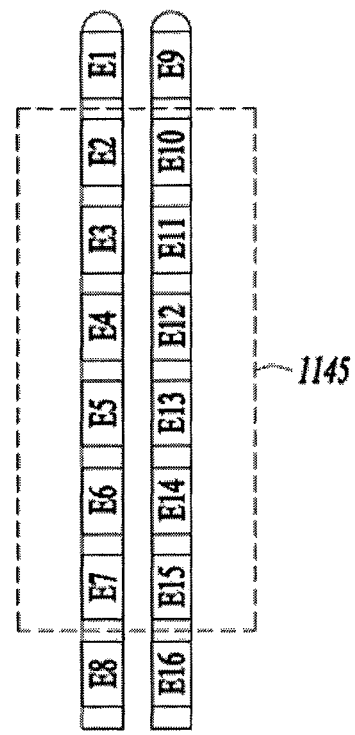
FIG. 11A  FIG. 11B

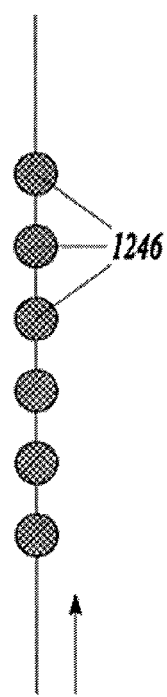
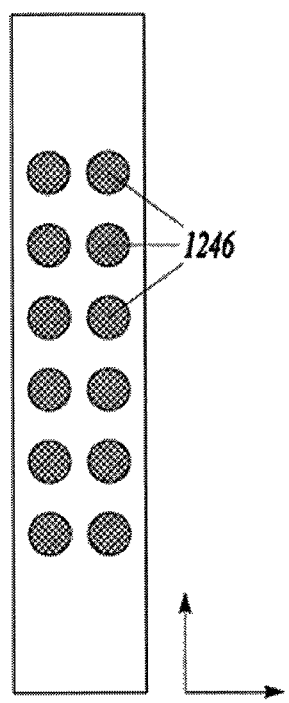
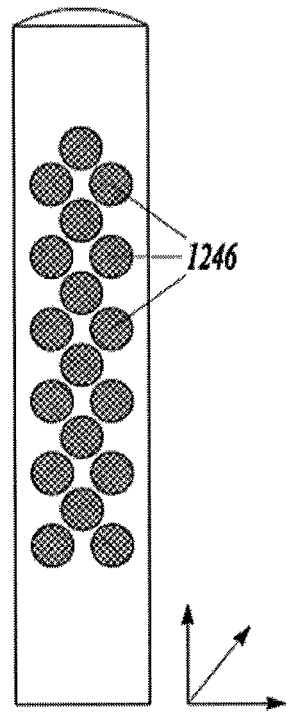
*FIG. 12A*    *FIG. 12B*    *FIG. 12C*

CUSTOMIZED TARGETED FIELDS FOR ELECTROTHERAPY APPLICATIONS

CLAIM OF PRIORITY

This application claims the benefit of priority under 35 U.S.C. § 119(e) of U.S. Provisional Patent Application Ser. No. 62/379,730, filed on Aug. 25, 2016, which is herein incorporated by reference in its entirety.

TECHNICAL FIELD

This document relates generally to medical devices, and more particularly, to systems, devices and methods for delivering neuromodulation.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Conventional SCS delivers electrical pulses to the dorsal column fibers in the dorsal aspect of the spinal cord, which in turn activate a set of inhibitory neurons in the dorsal horn, thereby masking the transmission of pain signals from the periphery of the body to the brain. Notably, the dorsal column fibers are organized in a spatially-dependent manner according to the region of the body with which they respectively interface. Accordingly, it is desirable to optimally target the neuromodulation to the precise fibers that correspond to the source of pain to be treated, while minimizing stimulation of other fibers in order to reduce or avoid side-effects.

However, it can be a challenge to find a desirable or optimal location (sweet-spot) for the neuromodulation field during programming of a neuromodulation device. Optimal-location searching involves a healthcare professional adjusting the targeting of the neuromodulation to provide optimal pain relief for the patient with minimal discomfort. State-of-the-art systems provide the ability to create complex electrode configurations to create virtual poles by combining fractionalized current output from physical electrodes in the vicinity of the desired virtual pole. Though beneficial for targeting specific areas, the complexity of adjusting multiple virtual poles to provide optimal neuromodulation for the patient presents a number of problems including extended duration of testing, and the possibility of causing patient discomfort during testing,

SUMMARY

The following examples illustrate various aspects of the embodiments described herein.

Example 1 is a neuromodulation customization system, comprising: a field definition user interface to facilitate entry of a customized electrotherapy field definition, the field definition user interface including a set of input controls for defining field shape, field intensity, and field steering parameters of the customized electrotherapy field; a neuromodulation signaling engine to produce commands for neuromodulation output circuitry to control generation of a customized electrotherapy field via a set of electrodes based on the customized electrotherapy field definition; and a supervisor engine to assess compliance of the customized electrotherapy field to be generated with applicable pre-defined criteria, and to modify generation of the customized electrotherapy field in response to an assessed non-compliance with the criteria.

In Example 2, the subject matter of Example 1 optionally includes wherein the field definition user interface, the neuromodulation signaling engine, and the supervisor engine are implemented on a programmer device that is adapted to be communicatively coupled to a neuromodulation device that includes the neuromodulation output circuitry.

In Example 3, the subject matter of Example 1 optionally includes wherein the supervisor engine is implemented on a neuromodulation device that includes the neuromodulation output circuitry.

In Example 4, the subject matter of Example 1 optionally includes wherein the supervisor engine is implemented on both, a programmer device that is adapted to be communicatively coupled to a neuromodulation device, and on the neuromodulation device.

In Example 5, the subject matter of any one or more of Examples 1-4 optionally include wherein the set of input controls includes graphical interactive virtual pole placement and intensity-setting controls, wherein operation of the virtual pole placement and intensity-setting controls defines the customized electrotherapy field.

In Example 6, the subject matter of any one or more of Examples 1-5 optionally include wherein the set of input controls includes graphical interactive field contour placement and intensity-setting controls, wherein operation of the field contour placement and intensity-setting controls defines the customized electrotherapy field.

In Example 7, the subject matter of any one or more of Examples 1-6 optionally include wherein the field definition interface includes a field shape library that includes previously-defined customized field definitions.

In Example 8, the subject matter of any one or more of Examples 1-7 optionally include wherein the field definition interface includes user-customized rules that impose a set of constraints of the customized electrotherapy field.

In Example 9, the subject matter of any one or more of Examples 1-8 optionally include wherein the field definition interface includes a set of steering-behavior controls that facilitate definition of permissible steering of the customized electrotherapy field.

In Example 10, the subject matter of Example 9 optionally includes wherein the steering-behavior controls include controls for defining translation, rotation, and deformation behavior of the customized electrotherapy field.

In Example 11, the subject matter of any one or more of Examples 1-10 optionally include wherein the neuromodulation signaling engine includes an electrode energy fractionalizer to access the customized field definition, and to generate control signaling for individually regulating electrical current to individual ones of the set of electrodes such that, collectively, the set of electrodes produces the customized electrotherapy field, wherein the control signaling is determined based on a combination of electrotherapy field modeling and application of heuristic rules.

In Example 12, the subject matter of any one or more of Examples 1-11 optionally include wherein the neuromodulation signaling engine includes a field sensor analyzer to receive measurements of field properties of an applied electrotherapy field, the measurements having been taken at a plurality of measurement locations, and to compare modeled field values at locations corresponding to the measurement locations to the field properties as measured.

In Example 13, the subject matter of any one or more of Examples 1-12 optionally include wherein the neuromodulation signaling engine includes an electrode contribution detector to measure an effectiveness of individual electrodes in producing the customized electrotherapy field.

In Example 14, the subject matter of any one or more of Examples 1-13 optionally include wherein the applicable predefined criteria includes patient safety rules that are nonspecific to the customized electrotherapy field, and user-defined field-behavior rules that are specific to the customized electrotherapy field.

In Example 15, the subject matter of any one or more of Examples 1-14 optionally include wherein the applicable predefined criteria includes exclusion zone rules that define areas from which the electrotherapy field is to be excluded.

In Example 16, the subject matter of any one or more of Examples 1-15 optionally include wherein the applicable predefined criteria includes physician-imposed rules that are nonspecific to the customized electrotherapy field.

In Example 17, the subject matter of any one or more of Examples 1-16 optionally include wherein the applicable predefined criteria includes constraints on a rate of change of electrotherapy field administration.

In Example 18, the subject matter of any one or more of Examples 1-17 optionally include an energy optimization engine to assess whether generation of the customized electrotherapy field includes any correctable energy inefficiencies, and to modify generation of the customized electrotherapy field to resolve one or more causes of the energy inefficiencies.

Example 19 is a method for customizing a neuromodulation field, the method comprising: providing a user interface having a set of input controls to accept a customized electrotherapy field definition, wherein the input controls include controls for defining field shape, field intensity, and field steering parameters of the customized electrotherapy field; producing commands for neuromodulation output circuitry to control generation of a customized electrotherapy field via a set of electrodes based on the customized electrotherapy field definition; assessing compliance of the customized electrotherapy field to be generated with applicable predefined criteria; and modifying generation of the customized electrotherapy field in response to an assessed noncompliance with the criteria.

In Example 20, the subject matter of Example 19 optionally includes wherein the input controls include steering-behavior controls that facilitate definition of permissible steering of the customized electrotherapy field.

In Example 21, the subject matter of any one or more of Examples 19-20 optionally include wherein producing the commands includes: accessing the customized field definition; and generating control signaling for individually regulating electrical current to individual ones of the set of electrodes such that, collectively, the set of electrodes produces the customized electrotherapy field, wherein the control signaling is determined based on a combination of electrotherapy field modeling and application of heuristic rules.

In Example 22, the subject matter of any one or more of Examples 19-21 optionally include receiving measurements of field properties of an applied electrotherapy field, the measurements having been taken at a plurality of measurement locations; and comparing modeled field values at locations corresponding to the measurement locations to the field properties as measured.

In Example 23, the subject matter of any one or more of Examples 19-22 optionally include measuring an effectiveness of individual electrodes in producing the customized electrotherapy field.

In Example 24, the subject matter of any one or more of Examples 19-23 optionally include wherein the applicable predefined criteria includes patient safety rules that are nonspecific to the customized electrotherapy field, and user-defined field-behavior rules that are specific to the customized electrotherapy field.

In Example 25, the subject matter of any one or more of Examples 19-24 optionally include wherein the applicable predefined criteria includes exclusion zone rules that define areas from which the electrotherapy field is to be excluded.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, some features of the neuromodulation leads and a pulse generator.

FIG. 8 is a schematic view of a single electrical neuromodulation lead implanted over approximately the longitudinal midline of the patient's spinal cord.

FIG. 9 illustrates an embodiment where an electrical neuromodulation lead has been implanted more laterally with respect to the spinal cord, thereby placing it proximate the dorsal horn of the spinal cord, and the other electrical neuromodulation lead has been implanted more medially with respect to the spinal cord, thereby placing it proximate the dorsal column of the spinal cord.

FIG. 10 illustrates a schematic view of the electrical neuromodulation lead showing an example of the fractionalization of the anodic current delivered to the electrodes on the electrical neuromodulation lead.

FIGS. 11A-11B illustrate, by way of example and not limitation, electrode arrangements and test regions of neural tissue along the electrode arrangements.

FIGS. 12A-12C illustrate, by way of example and not limitation, neural tissue locations that may be targeted within the test region in one, two and three dimensions, respectively.

DETAILED DESCRIPTION

Figure 1:
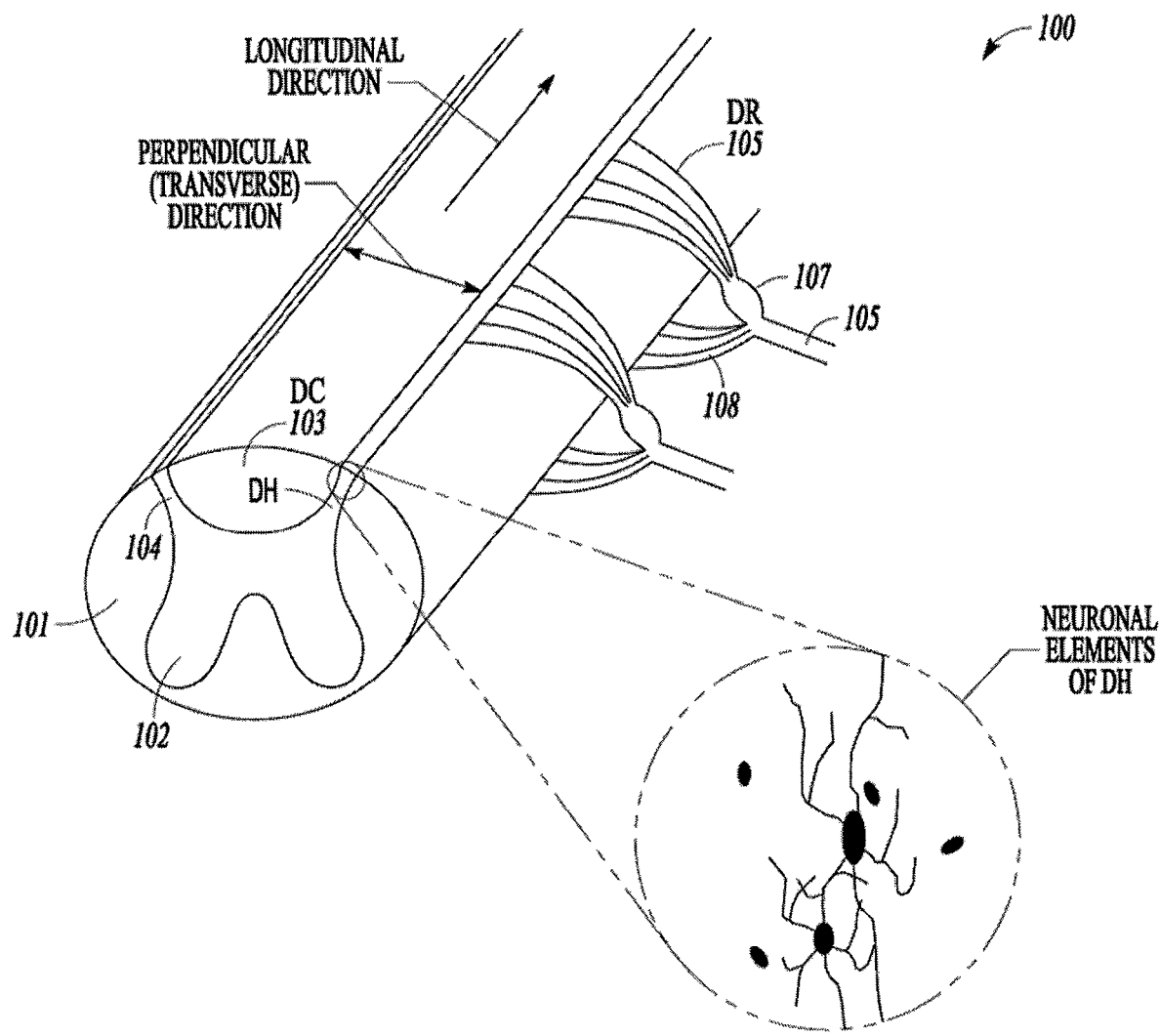
FIG. 1 illustrates a portion of a spinal cord.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Sub-perception neuromodulation is neuromodulation that can be therapeutically effective. Thus, the therapeutic effects of the sub-perception neuromodulation can be perceived. However, unlike conventional SCS therapy which can cause sensations (e.g. paresthesia) when the therapy is delivered, the energy of the delivered sub-perception neuromodulation field is not perceptible apart from any perceptible therapeutic effects.

Sub-perception SCS may typically have a wash-in period on the order of about one day. Thus, when the programmed neuromodulation parameters are changed to change the location of the neuromodulation field, the patient may not be able to determine the effect that the changes have on pain for a day or so. This makes it difficult quickly titrate the neuromodulation field of the sub-perception SCS to provide effective pain relief to the patient.

Various embodiments may be used to provide a faster therapeutic response (e.g. pain relief) to the sub-perception neuromodulation. Faster responses to sub-perception neuromodulation may be useful in order to find an effective location (sweet-spot) for the neuromodulation field within an office visit. The sweet spot may be a relatively optimal location for the neuromodulation field as it is more optimal than other locations tested.

Various embodiments may deliver a low intensity field in preparation for testing for and finding the sweet-spot for the sub-perception neuromodulation field. The preparatory, lower intensity field may be referred to herein as a priming field, as it is used to prime the neural tissue to induce a faster response to the sub-perception neuromodulation field. Thus, priming the neural tissue enables faster pain relief feedback from the patient during the search for the neuromodulation field sweet spot.

While priming neural tissue for purposes of testing sub-perception neuromodulation is specifically discussed as an example, priming neural tissue can be applied to lower the stimulation energy required for both sub-perception neuromodulation and supra-perception neuromodulation, and expedite the response to both test and therapeutic modulations. The energy of the supra-perception neuromodulation delivered to the neuromodulation field is perceptible. The therapeutic neuromodulation is delivered to treat a condition indicated for at least one type of neuromodulation. A test neuromodulation includes neuromodulation delivered for the purposes of testing effectiveness of a therapeutic neuromodulation and/or setting parameters for the therapeutic neuromodulation. For example, a patient suffering from certain types of pain may be indicated for spinal cord neuromodulation as the therapeutic neuromodulation. In similar fashion, a patient suffering from Parkinson's disease (PD), dystonia, essential tremor (ET), or other neurologic disorder of the brain may be indicated for DBS, such as subthalamic nucleus stimulation (STN) or globus pallidus internus (GPi) stimulation. A test neuromodulation may be delivered to find the sweet spot for the neuromodulation field and/or other parameters controlling delivery of the therapeutic neuromodulation, such as pulse waveform, pulse duration, pulse repetition rate, pulse amplitude, and the like. Depending on various factors such as patient preference and effectiveness, sub-perception neuromodulation and/or supra-perception neuromodulation may be delivered as the therapeutic neuromodulation. The target tissue of the neuromodulation can be primed for the test neuromodulation and/or the therapeutic neuromodulation. While specifically discussed for test neuromodulation delivered in preparation for therapeutic sub-perception neuromodulation, various embodiments can include applying the priming techniques (including timing of the priming relative to the therapeutic neuromodulation) discussed in this document to test neuromodulation delivered in preparation for therapeutic sub-perception neuromodulation, test neuromodulation delivered in preparation for therapeutic supra-perception neuromodulation, therapeutic sub-perception neuromodulation, and therapeutic supra-perception neuromodulation.

As some embodiments described herein involve Spinal Cord Stimulation (SCS, also referred to as spinal cord neuromodulation), a brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases.

Some embodiments deliver sub-perception therapy that is therapeutically effective to treat pain, for example, but the patient does not sense the delivery of the neuromodulation field (e.g. paresthesia). Sub-perception therapy may be provided using higher frequency neuromodulation (e.g. about 1500 Hz or above) of the spinal cord. Sub-perception neuromodulation may also be provided through neuromodulation field shaping (e.g., using multiple independent current control, or MICC), and temporal shaping of pulse train (e.g., burst, longer pulses). It appears that these higher frequencies may effectively block the transmission of pain signals in the afferent fibers in the DC. Some embodiments herein selectively modulate DH tissue or DR tissue over DC tissue to provide sub-perception therapy. Such selective neuromodulation may be delivered at lower frequencies. For example, the selective neuromodulation may be delivered at frequencies less than 1,200 Hz. The selective neuromodulation may be delivered at frequencies less than 1,000 Hz in some embodiments. In some embodiments, the selective neuromodulation may be delivered at frequencies less than 500 Hz. In some embodiments, the selective neuromodulation may be delivered at frequencies less than 350 Hz. In some embodiments, the selective neuromodulation may be delivered at frequencies less than 130 Hz. The selective neuromodulation may be delivered at low frequencies (e.g. as low as 2 Hz). The selective neuromodulation may be delivered even without pulses (e.g. 0 Hz) to modulate some neural tissue. By way of example and not limitation, the selective neuromodulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective neuromodulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

While SCS is specifically discussed as an example of neuromodulation therapy, various embodiments can also include applying the priming techniques including timing of delivery discussed in this document to Peripheral Nerve Stimulation (PNS) therapies. For example, sub-perception PNS may be applied to alleviate pain. Various embodiments include priming the neural tissue at target locations for delivering the neuromodulation where required intensity of the neuromodulation for testing and/or therapeutic purposes may be lowered.

Figure 2:
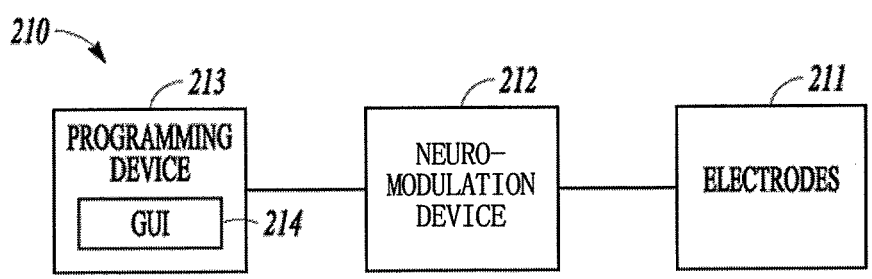
FIG. 2 illustrates, by way of example, an embodiment of a neuromodulation system.

FIG. 2 illustrates an embodiment of a neuromodulation system. The illustrated system 210 includes electrodes 211, a neuromodulation device 212, and a programming device 213. The electrodes 211 are configured to be placed on or near one or more neural targets in a patient. The electrodes 211 may form part of an electrode arrangement. The neuromodulation device 212 is configured to be electrically connected to electrodes 211 and deliver neuromodulation energy, such as in the form of electrical pulses, to the one or more neural targets though electrodes 211. The delivery of the neuromodulation is controlled using a plurality of neuromodulation parameters, such as neuromodulation parameters specifying the electrical pulses and a selection of electrodes through which each of the electrical pulses is delivered. In various embodiments, at least some parameters of the plurality of neuromodulation parameters are programmable by a user, such as a physician or other caregiver. The programming device 213 provides the user with accessibility to the user-programmable parameters. In various embodiments, the programming device 213 is configured to be communicatively coupled to neuromodulation device via a wired or wireless link. In various embodiments, the programming device 213 includes a graphical user interface (GUI) 214 that allows the user to set and/or adjust values of the user-programmable neuromodulation parameters.

In various embodiments, the neuromodulation system 210 can include implantable and external elements. For example, the neuromodulation device 212 can be an implantable neuromodulation device, the electrodes 211 can include electrodes in one or more implantable lead and/or the implantable neuromodulation device, and the programming device can be an external programming device configured to be communicatively coupled to the implantable neuromodulation device via telemetry, as further discussed with reference to FIGS. 5 and 6. In another example, the neuromodulation device 212 can be an external neuromodulation device such as a Transcutaneous Electrical Neural Stimulation (TENS) device, the electrodes 211 can include surface electrodes such as skin patch electrodes, and the programming device can be an external programming device configured to be communicatively coupled to the implantable neuromodulation device via a wired or wireless link, or integrated with the external neuromodulation device. In still another example, the neuromodulation device 212 can be an external neuromodulation device, the electrodes 211 can include percutaneous electrodes, and the programming device can be an external programming device configured to be communicatively coupled to the implantable neuromodulation device via a wired or wireless link, or integrated with the external neuromodulation device. In various embodiments, an external neuromodulation device with surface and/or percutaneous electrodes can be used, for example, for delivering a test neuromodulation, delivering a therapeutic neuromodulation during a trial period, and delivering a short-term therapeutic neuromodulation.

In one embodiment, an external neuromodulation device with surface electrodes can be used during a trial period prior to a potential implantation of an implantable SCS system. A skin patch including the surface electrodes is placed over the patient's spine near the region where percutaneous electrodes will be placed for use during the trial period. The external neuromodulation device such as a dedicated External Trial Stimulator (ETC) and/or an external TENS device is used to prime the neural tissue before the trial period using one or more electrodes selected from the surface electrodes. This allows the programming of the external neuromodulation device for delivering therapeutic neuromodulation through the percutaneous electrodes to be performed with reduced wash-in time, such as immediately following the placement of the percutaneous electrodes.

Figure 3:
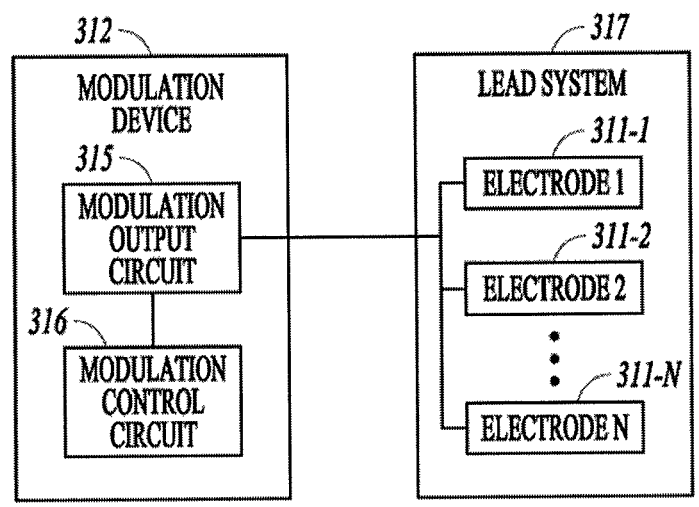
FIG. 3 illustrates, by way of example, an embodiment of a neuromodulation device, such as may be implemented in the neuromodulation system of FIG. 2.

FIG. 3 illustrates an embodiment of a neuromodulation device 312, such as may be implemented in the neuromodulation system 210 of FIG. 2. The illustrated embodiment of the neuromodulation device 312 includes a neuromodulation output circuit 315 and a neuromodulation control circuit 316. Those of ordinary skill in the art will understand that the neuromodulation device 312 may include additional components such as sensing circuitry for patient monitoring and/or feedback control of the therapy, telemetry circuitry and power. The neuromodulation output circuit 315 produces and delivers neuromodulation pulses. The neuromodulation control circuit 316 controls the delivery of the neuromodulation pulses using the plurality of neuromodulation parameters. The combination of the neuromodulation output circuit 315 and neuromodulation control circuit 316 may collectively be referred to as a pulse generator. The lead system 317 includes one or more leads each configured to be electrically connected to neuromodulation device 312 and a plurality of electrodes 311-1 to 311-N (where N≥2) distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between neuromodulation output circuit 315 and tissue of the patient. The neuromodulation pulses are each delivered from the neuromodulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue, brain tissue, or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "neuromodulation parameter set." Each set of neuromodulation parameters, including fractionalized current distribution to the electrodes (as percentage cathodic current, percentage anodic current, or off), may be stored and combined into a neuromodulation program that can then be used to modulate multiple regions within the patient.

The number of electrodes available combined with the ability to generate a variety of complex electrical pulses, presents a huge selection of neuromodulation parameter sets to the clinician or patient. For example, if the neuromodulation system to be programmed has sixteen electrodes, millions of neuromodulation parameter sets may be available for programming into the neuromodulation system. Furthermore, for example SCS systems may have thirty-two electrodes which exponentially increases the number of neuromodulation parameters sets available for programming. To facilitate such selection, the clinician generally programs the neuromodulation parameters sets through a computerized programming system to allow the optimum neuromodulation parameters to be determined based on patient feedback or other means and to subsequently program the desired neuromodulation parameter sets.

Conventional programming for SCS therapy uses paresthesia to select an appropriate neuromodulation parameter set. The paresthesia induced by the neuromodulation and perceived by the patient should be located in approximately the same place in the patient's body as the pain that is the target of treatment. When leads are implanted within the patient, an operating room (OR) mapping procedure may be performed to apply electrical neuromodulation to test placement of the leads and/or electrodes, thereby assuring that the leads and/or electrodes are implanted in effective locations within the patient. According to various embodiments, programming for sub-perception neuromodulation may prime the neural tissue to provide faster response times to the sub-perception neuromodulation as part of an OR mapping procedure.

Once the leads are correctly positioned, a fitting procedure, which may be referred to as a navigation session, may be performed to program the external control device, and if applicable the neuromodulation device, with a set of neuromodulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the neuromodulation energy away from the target site. By reprogramming the neuromodulation device (typically by independently varying the neuromodulation energy on the electrodes), the VOA can often be moved back to the effective pain site without having to re-operate on the patient in order to reposition the lead and its electrode array. According to various embodiments, a navigation session for sub-perception neuromodulation may prime the neural tissue to provide faster response times to the sub-perception neuromodulation.

Although various embodiments described in this document prime neural tissue to provide faster responses to sub-perception neuromodulation in order to perform faster OR mapping or navigation sessions, the present subject matter is not limited to such programming. By way of example and not limitation, some embodiment may prime the neural tissue before delivering the sub-perception neuromodulation therapy to the neural tissue simply to reduce the wash-in time of the therapy. Thus, by way of example, a patient may obtain pain relief much quicker with the primed neural tissue than without the primed neural tissue.

Figure 4:
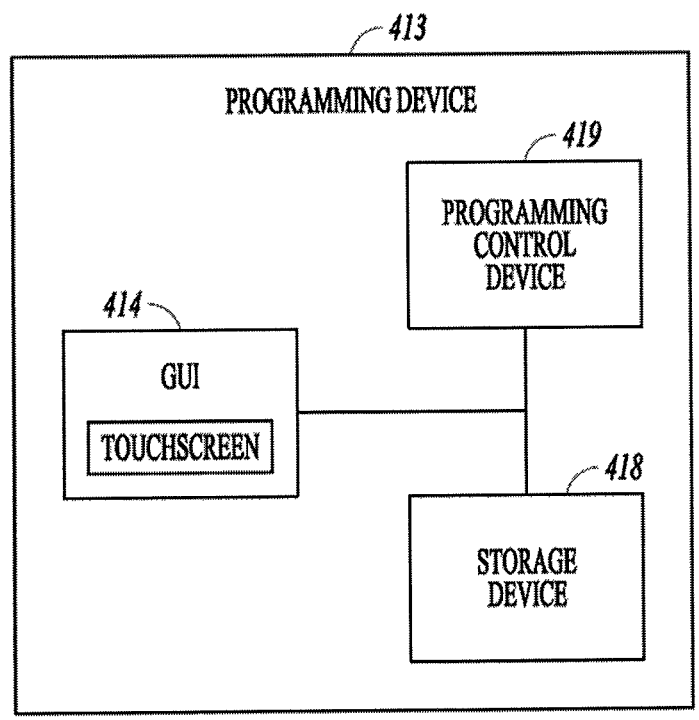
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of neuromodulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the neuromodulation parameters, such as touchscreen, keyboard, keypad, touchpad, trackball, joystick, and mouse. The storage device 418 may store, among other things, neuromodulation parameters to be programmed into the neuromodulation device. The programming device 413 may transmit the plurality of neuromodulation parameters to the neuromodulation device. In some embodiments, the programming device 413 may transmit power to the neuromodulation device. The programming control circuit 419 may generate the plurality of neuromodulation parameters. In various embodiments, the programming control circuit 419 may check values of the plurality of neuromodulation parameters against safety rules to limit these values within constraints of the safety rules.

In various embodiments, circuits of neuromodulation, including its various embodiments discussed in this document, may be implemented using a combination of hardware, software and firmware. For example, the circuit of a GUI, neuromodulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
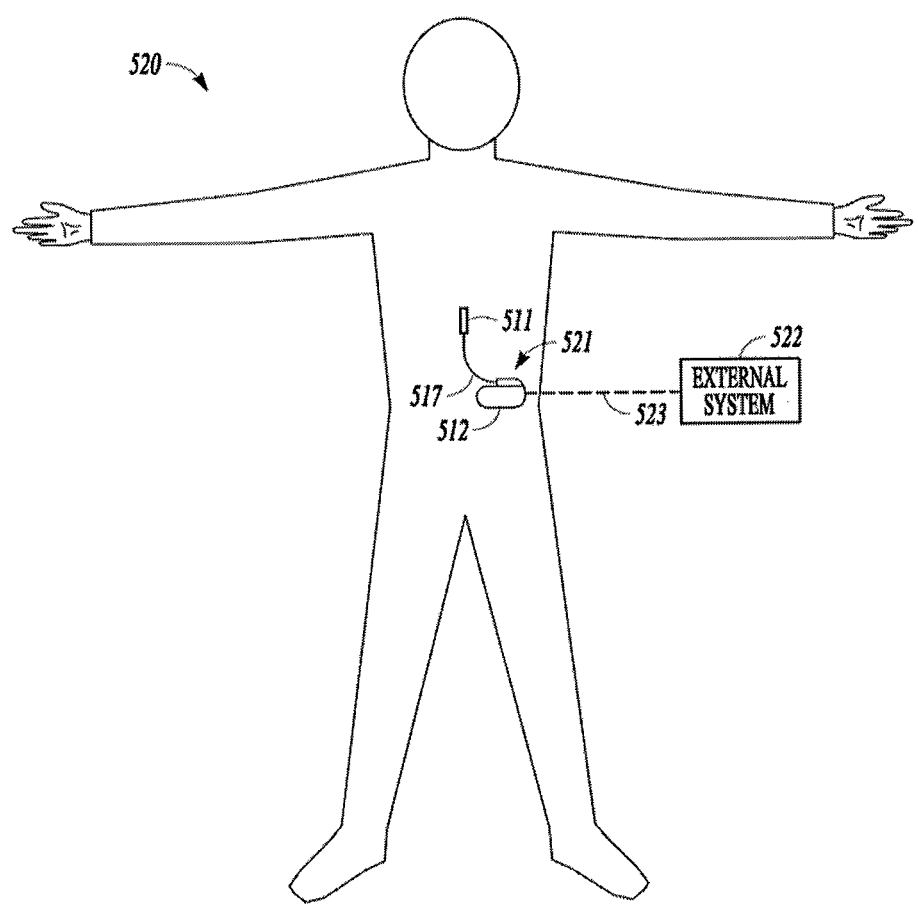
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets such as may be useful for delivering other therapies. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable neuromodulation device (also referred to as an implantable pulse generator, or IPG) 512, a lead system 517, and electrodes 511. The lead system 517 includes one or more leads each configured to be electrically connected to the neuromodulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of neuromodulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable neuromodulation device 512 may be implanted in a surgically-made pocket either in the abdomen or above the buttocks, or may be implanted in other locations of the patient's body. The lead extension(s) may be used to facilitate the implantation of the implantable neuromodulation device 512 away from the exit point of the neuromodulation lead(s).

Figure 6:
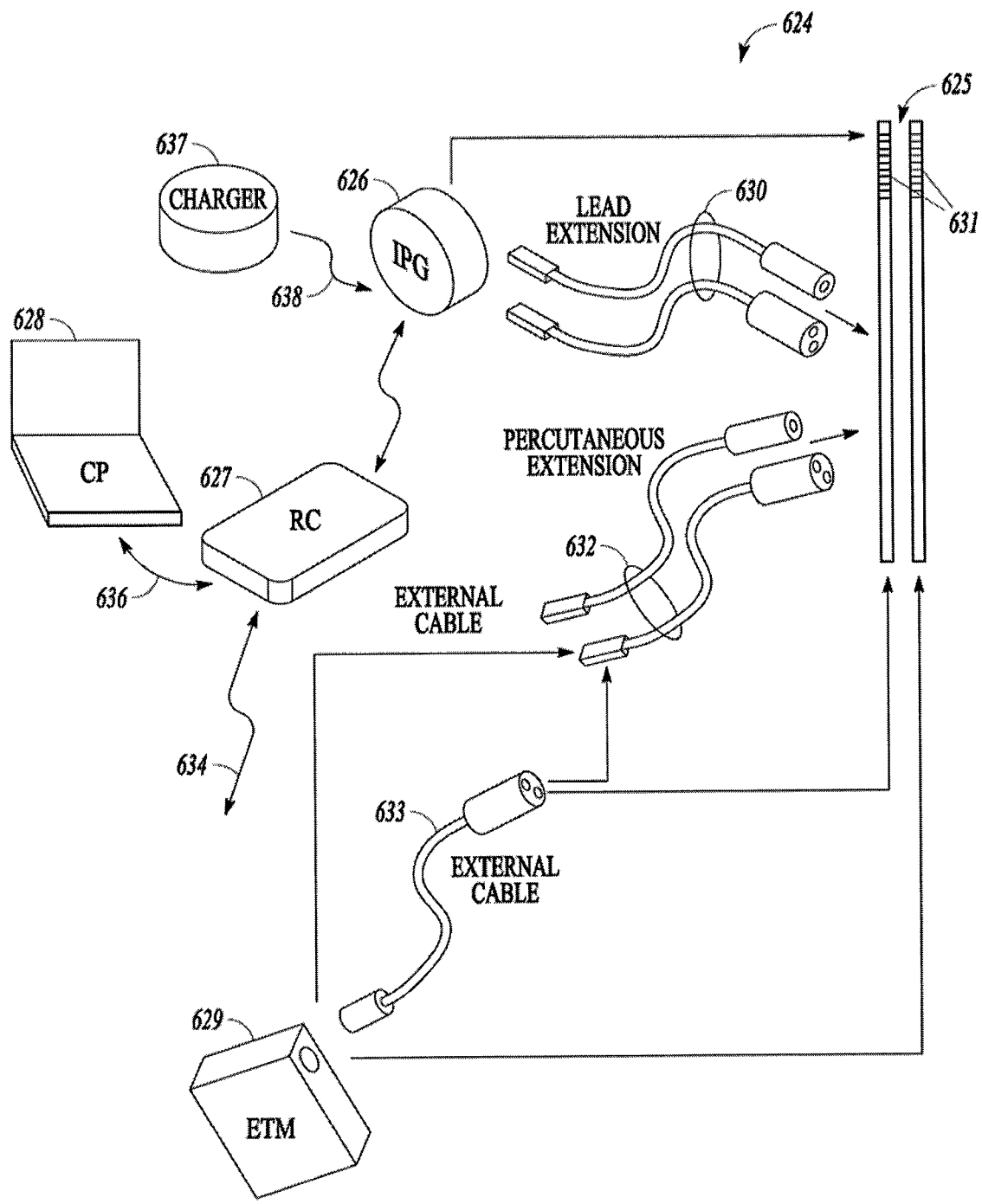
FIG. 6 illustrates, by way of example, an embodiment of a Spinal Cord Stimulation (SCS) system, which also may be referred to as a Spinal Cord Neuromodulation (SCM) system.

FIG. 6 illustrates, by way of example, an embodiment of a SCS system, which also may be referred to as a Spinal Cord Neuromodulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry, also referred to as a pulse generator, that delivers electrical neuromodulation energy in the form of a pulsed electrical waveform (i.e., a temporal series of electrical pulses) to the electrodes in accordance with a set of neuromodulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical neuromodulation energy to the electrodes accordance with a set of neuromodulation parameters. The ETM 629 is a non-implantable device that is used on a trial basis after the neuromodulation leads 625 have been implanted and prior to implantation of the IPG 626, to test the responsiveness of the neuromodulation that is to be provided. Functions described herein with respect to the IPG 626 can likewise be performed with respect to the ETM 629.

The RC 627 may be used to telemetrically control the ETM 629 via a bi-directional RF communications link 634. The RC 627 may be used to telemetrically control the IPG 626 via a bi-directional RF communications link 635. Such control allows the IPG 626 to be turned on or off and to be programmed with different neuromodulation parameter sets. The IPG 626 may also be operated to modify the programmed neuromodulation parameters to actively control the characteristics of the electrical neuromodulation energy output by the IPG 626. A clinician may use the CP 628 to program neuromodulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed neuromodulation parameters provided by the CP 628 may also be used to program the RC 627, so that the neuromodulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical neuromodulation generated by the IPG 626 to allow the desired parameters to be determined based on patient feedback or other feedback and for subsequently programming the IPG 626 with the desired neuromodulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical neuromodulation energy output by the neuromodulation leads, and select and program the IPG with neuromodulation parameters in both a surgical setting and a clinical setting.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, neuromodulation output circuitry, and other suitable components known to those skilled in the art. The microcontroller executes a suitable program stored in memory, for directing and controlling the neuromodulation performed by IPG.

Electrical neuromodulation energy is provided to the electrodes in accordance with a set of neuromodulation parameters programmed into the pulse generator. The electrical neuromodulation energy may be in the form of a pulsed electrical waveform. Such neuromodulation parameters may comprise electrode combinations, which define the electrodes that are activated as anodes (positive), cathodes (negative), and turned off (zero), percentage of neuromodulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the neuromodulation on duration X and neuromodulation off duration Y). The electrical pulse parameters may define an intermittent neuromodulation with "on" periods of time where a train of two or more pulses are delivered and "off" periods of time where pulses are not delivered. Electrodes that are selected to transmit or receive electrical energy are referred to herein as "activated," while electrodes that are not selected to transmit or receive electrical energy are referred to herein as "non-activated."

Electrical neuromodulation occurs between or among a plurality of activated electrodes, one of which may be the IPG case. The system may be capable of transmitting neuromodulation energy to the tissue in a monopolar or multipolar (e.g., bipolar, tripolar, etc.) fashion. Monopolar neuromodulation occurs when a selected one of the lead electrodes is activated along with the case of the IPG, so that neuromodulation energy is transmitted between the selected electrode and case.

Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical neuromodulation energy that is therapeutically effective and causes the patient to perceive delivery of the energy (e.g. therapeutically effective to relieve pain with perceived paresthesia), and may be operated in a sub-perception mode to deliver electrical neuromodulation energy that is therapeutically effective and does not cause the patient to perceive delivery of the energy (e.g. therapeutically effective to relieve pain without perceived paresthesia). Some embodiments may use one channel to prime the neural tissue with a sub-perception neuromodulation field, and use another channel to deliver therapeutic sub-perception neuromodulation to the neural tissue.

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

FIG. 8 is a schematic view of a single electrical neuromodulation lead 839 implanted over approximately the longitudinal midline of the patient's spinal cord 840. FIG. 9 illustrates an embodiment where an electrical neuromodulation lead 941 has been implanted more laterally with respect to the spinal cord, thereby placing it proximate the dorsal horn of the spinal cord, and the other electrical neuromodulation lead 942 has been implanted more medially with respect to the spinal cord, thereby placing it proximate the dorsal column of the spinal cord 940.

It is understood that additional leads or lead paddle(s) may be used, such as may be used to provide a wider electrode arrangement and/or to provide the electrodes closer to dorsal horn elements, and that these electrode arrays also may implement fractionalized current.

Placement of the lead more proximate to the DH than the DC may be desirable to preferentially stimulate DH elements over DC neural elements for a sub-perception therapy. Lead placement may also enable preferential neuromodulation of dorsal roots over other neural elements. Any other plurality of leads or a multiple column paddle lead can also be used. Longitudinal component of the electrical field is directed along the y-axis depicted in FIG. 8, and a transverse component of the electrical field is directed along the x-axis depicted in FIG. 8.

FIG. 10 is a schematic view of the electrical neuromodulation lead 1043 showing an example of the fractionalization of the anodic current delivered to the electrodes on the electrical neuromodulation lead. These figures illustrate fractionalization using monopolar neuromodulation where a case electrode of the IPG is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical neuromodulation. Also, the ends of the portion of the electrical neuromodulation lead include electrodes having lower gradient in the longitudinal direction. The magnitude of the electrical field tapers down at the ends of the electrical neuromodulation lead. Fractionalization of the current may accommodate variation in the tissue underlying those electrodes. The fractionalization across the electrical neuromodulation lead can vary in any manner as long as the total of fractionalized currents equals 100%. Various embodiments described herein implement a programmed algorithm to determine the appropriate fractionalization to achieve a desired neuromodulation field property.

Neuromodulation thresholds vary from patient to patient and from electrode to electrode within a patient. An electrode/tissue coupling calibration of the electrodes may be performed to account for these different neuromodulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the neuromodulation signal strength of the electrical pulse train delivered when the control element is actuated. Other sensed parameter or patient-perceived neuromodulation values (e.g. constant paresthesia, or maximum tolerable paresthesia) may be used to provide the electrode/tissue coupling calibration of the electrodes.

The SCS system may be configured to deliver different electrical fields to achieve a temporal summation of neuromodulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

Some embodiments are configured to determine a neuromodulation parameter set to create a field shape to provide a broad and uniform neuromodulation field such as may be useful to prime targeted neural tissue with sub-perception neuromodulation. Some embodiments are configured to determine a neuromodulation parameter set to create a field shape to reduce or minimize neuromodulation of non-targeted tissue (e.g. DC tissue). The neuromodulation field may be shaped by using multiple independent current control (MICC) or multiple independent voltage control to guide the estimate of current fractionalization among multiple electrodes and estimate a total amplitude that provide a desired strength. For example, the neuromodulation field may be shaped to enhance the neuromodulation of DH neural tissue and to minimize the neuromodulation of DC tissue. A benefit of MICC is that MICC accounts for various in electrode-tissue coupling efficiency and perception threshold at each individual contact, so that "hot-spot" stimulation is eliminated.

Sub-perception SCS typically does not provide a quick feedback response regarding the effectiveness of the therapy. Rather, it has been observed that a wash-in period (a period of time for a delivered therapy to be therapeutically effective) for the sub-perception SCS is typically about one day. Thus, when the programmed neuromodulation parameters are changed to change the location of the sub-perception neuromodulation field, the patient may not be able to determine the effect that the changes have (e.g. pain relief) for a day or so. This make it difficult quickly titrate the neuromodulation field of the sub-perception SCS to provide effective pain relief to the patient.

It has been observed during research that priming the neural tissue enables faster pain relief feedback from the patient during the search for the neuromodulation field sweet spot. It may be appropriate to consider that priming the neural tissue "warms up" the neural tissue in a manner that reduces the wash-in time. However, neural physiology is complex and it is not currently understood why the primed neural tissue reduces the wash-in time of the sub-perception therapy such that the patient can quickly feel pain relief. It is noted that "priming" is different than conditioning pre-pulses which are delivered immediately before the neuromodulation pulse. A conditioning pre-pulse is timed to make a nerve more susceptible or less susceptible to capture by the immediately subsequent neuromodulation pulse. Thus, a conditioning pre-pulse has a specific relationship to a neuromodulation pulse. In contrast, the prime neuromodulation field extends over a much longer period of time. Further, rather than making neural tissue more or less excitable by a pulse, the prime neuromodulation field reduces a wash-in time of a therapy to make a patient feel the effects of the therapy (e.g. pain relief) much more quickly than would be felt without the prime field.

Various embodiments may deliver a low intensity, neuromodulation field in preparation to test for and find the sweet-spot for the neuromodulation field. The preparatory, lower intensity field is referred to herein as a prime field, as it is used to prime the neural tissue to be tested to have a quicker response to during the testing for the neuromodulation sweet spot for pain relief. The prime field can be a supra-perception or sub-perception neuromodulation field, but is typically even lower than the therapeutic sub-perception neuromodulation field.

A test region of neural tissue represents a region of tissue that is to be tested for a sweet spot. The test region may include many potential locations for targeting the neuromodulation field. The test region may span along the entire electrode arrangement (e.g. lead(s)) or may be reduced to a portion of the electrode arrangement. Priming may also be applied in a trolling fashion to cover the entire test region. As it is not known what location is to be most effective, the entire test region is primed.

In a non-limiting example to illustrate the lower intensity of the prime neuromodulation field, one may assume that a patient may feel paresthesia or otherwise perceive the delivery of the neuromodulation field when the neuromodulation current has an amplitude of 10 mA. Thus, 10 mA may be considered to be a perception threshold for the neuromodulation. Therapeutic sub-perception neuromodulation may be delivered within a range of 30% to 90% of the perception threshold. Thus, in this example, neuromodulation with an amplitude between 3 mA and 9 mA may be therapeutically effective (e.g. provide pain relief). Priming the neural tissue may be accomplished using amplitudes near the lower range of the sub-perception neuromodulation or even below the lower range of the sub-perception neuromodulation such as, by way of example, between 2 mA to 4 mA. The sub-perception neuromodulation affects the neural tissue, but not to the point where the neuromodulation induces the nerve to trigger action potentials. Thus, the prime field may affect the ion concentrations within and outside of the neural pathways responsible for pain relief and/or may affect neurotransmitters responsible for pain relief, such that additional changes by sub-perception neuromodulation may more quickly induce desirable action potentials in these neural pathways responsible for pain relief.

FIGS. 11A-11B illustrate, by way of example and not limitation, electrode arrangements (e.g. E1-E8 in FIG. 11A and E1-E16 in FIG. 11B) and test regions 1145 of neural tissue along the electrode arrangements. These test regions 1145 may extend across the entire electrode arrangement. In some embodiments, the test regions may extend along only a portion of the electrode arrangement. By way of example, some embodiments may allow a user to select the test region and thus select the portion of the electrode arrangement to be tested. In the example illustrated in FIG. 11A the test region is neural tissue along the E2 to E7 electrodes, and in the example illustrated in FIG. 11B the test region is neural tissue along the E2 through E7 and the E10 to E15 electrodes.

The electrodes in the electrode arrangement may be fractionalized, using different neuromodulation parameter sets, to change the portion of the neural tissue that is modulated. Thus, there may be many neural tissue locations that can be targeted with the test region of neural tissue adjacent to the electrode arrangement. FIGS. 12A-12C illustrate, by way of example and not limitation, neural tissue locations 1246 that may be targeted within the test region in one, two and three dimensions, respectively. In the one-dimensional example illustrated in FIG. 12A, the neural locations that may be targeted may simply be a line of potential targets such as may be observed from a single lead with a linear arrangement of electrodes. In the two dimensional example illustrated in FIG. 12B the neural locations that may be targeted may be considered to lie in a plane proximate to the electrode arrangement. In the three-dimensional example illustrated in FIG. 12C, the neural locations that may be targeted may be considered to be a volume of tissue proximate to the electrode arrangement. By way of example, the two-dimensional and three-dimensional test regions may be implemented using two or more leads of electrodes. Thus, the test regions may be relatively simple or complex shapes, and may include relatively few or relatively many locations to be tested.

Figure 13:
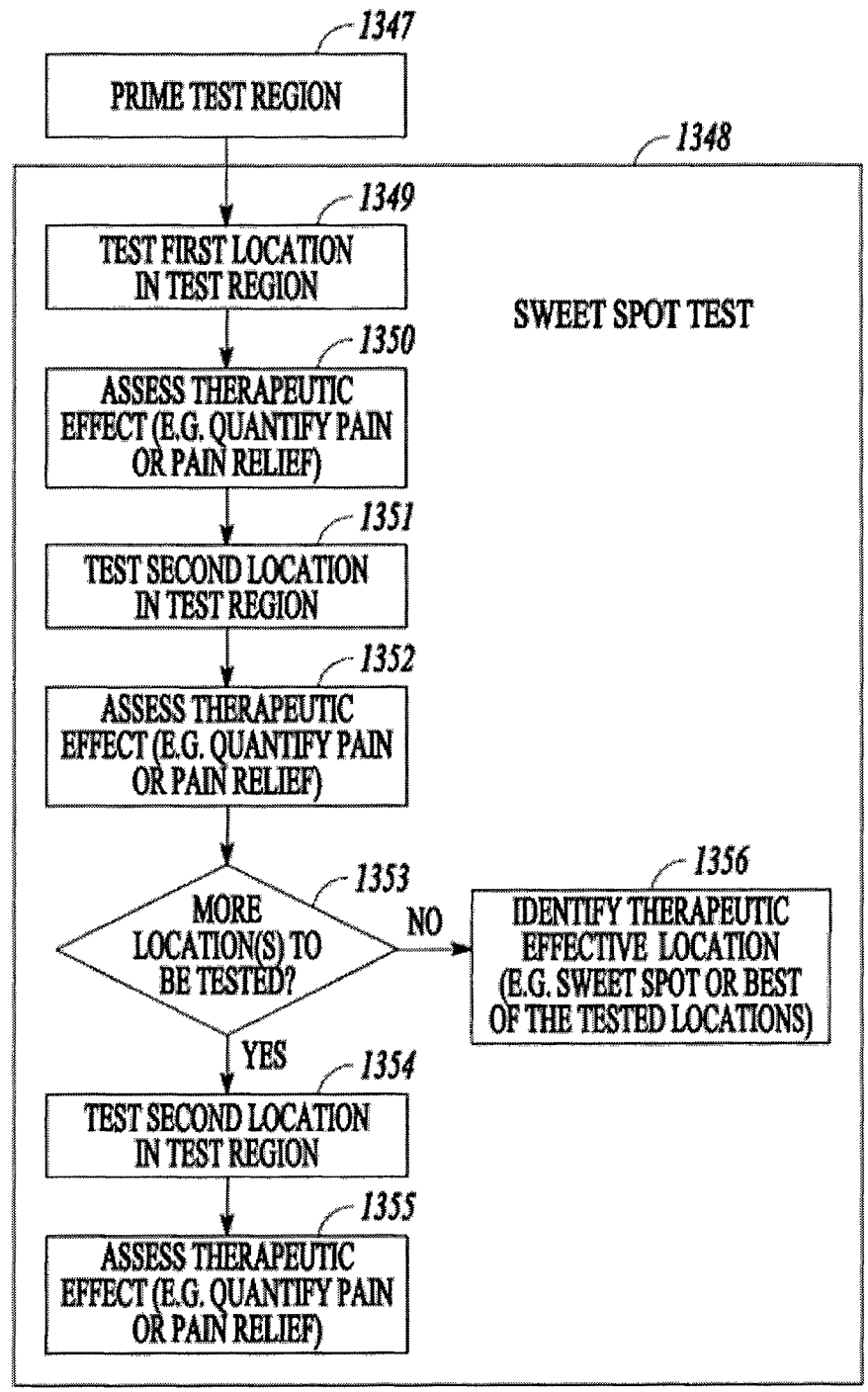
FIG. 13 illustrates an example of a method for finding a sweet spot for sub-perception neuromodulation.

FIG. 13 illustrates an example of a method for finding a sweet spot for sub-perception neuromodulation. In the illustrated example, a test region is primed with the sub-perception neuromodulation field 1347, and the sweet-spot test is performed 1348 to find location of neural tissue that is therapeutically effective when targeted with sub-perception neuromodulation. The sweet spot test may involve a manual process to reprogram the neuromodulation field parameter set with different values to change the targeted location of the neuromodulation field. In some embodiments of the test, the targeted location is automatically changed (e.g. trolled)

by automatically changing values of the neuromodulation field parameter set. Some embodiments may semi-automatically change values of the neuromodulation field parameter set to change the targeted location of the neuromodulation field.

At 1349, a first location in the test region is tested by focusing the neuromodulation field onto the first location. At 1350, the therapeutic effect of modulating the first location is assessed. In an example where the therapy is a therapy to alleviate pain, the patient may provide this assessment by quantifying a level of pain or level of pain relief that they are experiencing. In some examples, a biomarker is used to provide an assessment of the therapeutic efficacy of the neuromodulation field focused on the tested location. At 1351, the neuromodulation field parameter set is changed to change the focus of the neuromodulation field to test a second location in the test region. At 1352, the therapeutic effect of modulating the second location is assessed. If more location(s) are to be tested, as illustrated at 1353, the process may continue to 1354 to test the next location and to 1355 to assess the therapeutic effect of the next location. The process may determine or identify the location(s) that are therapeutically effective 1356 by evaluating the quantified effects of the therapy. In some embodiments, the quantified effects may be compared to each other to identify the tested location that has the best therapeutic effect (the sweet spot) or one of the best therapeutic effects (a sweet spot).

The present subject matter may be used to test relatively small locations using a more narrowly focused neuromodulation field such as generally illustrated above in FIGS. 12A-12C, or may be used to test relatively larger locations of neural tissue using a more uniform (less focused) neuromodulation field. The test of larger locations may be followed by a more focused test or tests within one of the larger location. Regardless of whether the test location is relatively large or relatively small, the present subject matter primes the test neural tissue to reduce a wash-in time of the therapy and enable a quick assessment of the effectiveness of the therapy. A few search algorithms are provided below as examples. Other processes for testing locations of neural tissue are possible.

Various embodiments start with full-lead then use a search algorithm to reduce the span and improve energy efficiency. This can be done from the RC or CP, or in the IPG with RC feedback. The proposed algorithms may rely on some form of feedback indicating the effectiveness of the neuromodulation. For example, a patient may provide feedback regarding pain relief. Feedback may also provide a biomarker signal.

The system may include a routine to confirm that the neuromodulation along the full lead is effective and then focus the neuromodulation along a portion of the lead. Thus, for example, a generally uniform neuromodulation field may be provided along this smaller portion of the lead. This field is still broad as it may be provided across an area with multiple electrode contacts, but it is less than the entire electrode arrangement using electrode array(s) on the lead (s).

Various embodiments may provide a rostra-caudal focus routine that includes a binary search routine. The binary search routine segments the lead or array of electrodes from a full set of electrodes into at least two subsets of electrodes that defines partial lead search regions. The binary search routine may confirm that neuromodulation along the full lead is effective.

Figure 14:
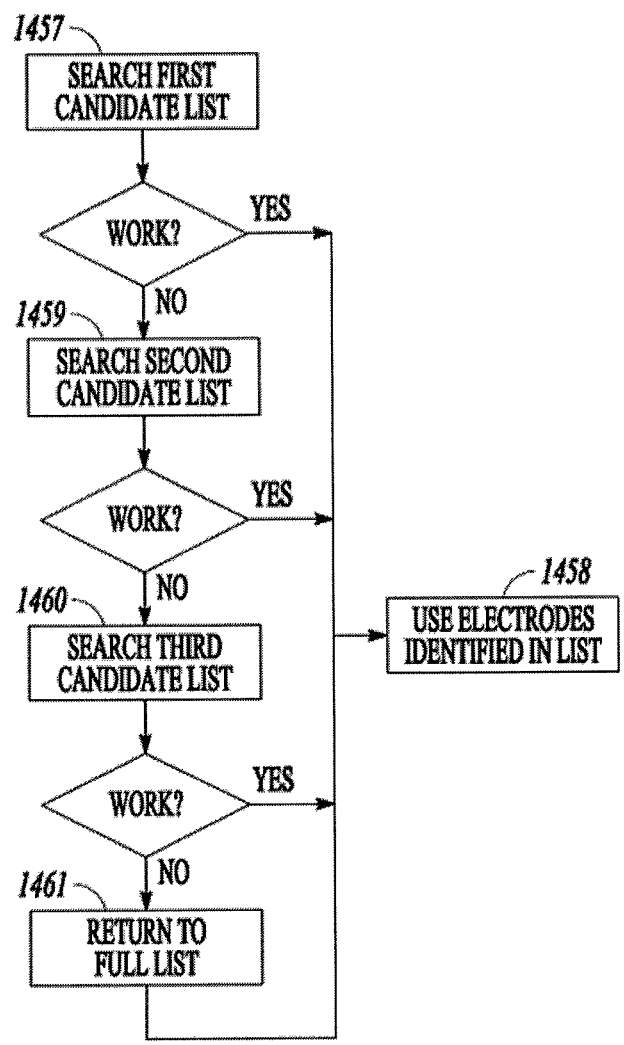
FIG. 14 illustrates, by way of example, aspects of a binary search routine as a rostra-caudal focus routine.

FIG. 14 illustrates, by way of example, aspects of a binary search routine as a rostra-caudal focus routine. A first subset of electrodes that define a first partial lead search region can be tested to determine if the neuromodulation is effective using the first subset 1457. If it is effective, the first subset of electrodes that define the first partial lead search region may be used to deliver the neuromodulation 1458 or for further more focused tests. If it is not effective, then a second subset of electrodes that define a second partial lead search region may be tested to determine if the second subset of electrodes is effective 1459. If it is effective, the second subset of electrodes that define the second partial lead search region may be used to deliver the neuromodulation 1458. If it is not effective, then a third (or nth) subset of electrodes that define a third (or nth) partial lead search region may be tested to determine if the third (or nth) subset of electrodes is effective 1460. If it is effective, the third (or nth) subset of electrodes that define the third (or nth) partial lead search region may be used to deliver the neuromodulation 1458. If it is not effective, then the binary search process may return to the full list of electrodes 1461 which was previously determined to be effective. At least some of the subsets of electrodes may be exclusive of each other. At least some of the subsets of electrodes may intersect with each other. In some embodiments, at least two subsets are exclusive, and at least one subset has an intersection with another subset.

Figure 15:
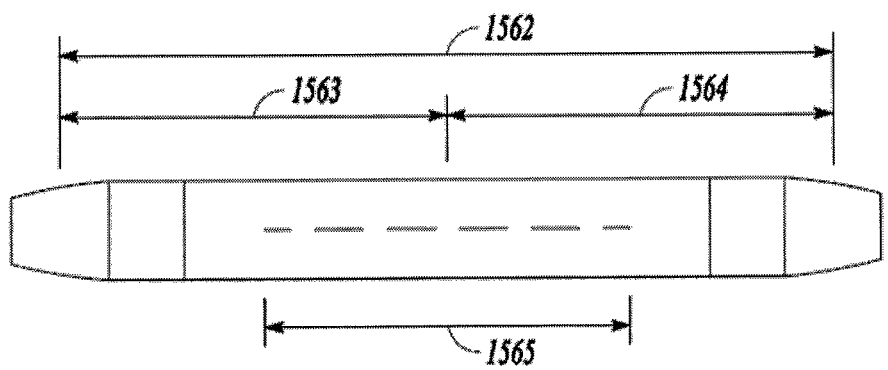
FIG. 15 illustrates an example of the binary search routine.

FIG. 15 illustrates an example of the binary search routine. The lead has a full span 1562 which may be split into three partial lead search regions 1563, 1564 and 1565, each partial search region including a corresponding subset of electrodes. By way of example and not limitation, the first and second subsets 1563 and 1564 of electrodes may be mutually exclusive, and third subset 1565 may include an intersection with the first subset and also may include an intersection with the second set. In an example, the full lead may be bifurcated to provide the first partial lead search region 1563 on a first side of the lead (e.g. left end of electrode array to middle) and the second partial lead search region 1564 on a second side of the lead (e.g. right end of the electrode array to middle). The third partial lead search region 1565 may partially overlap each of the first and second partial lead search regions. Thus, the partial lead search regions may define a first end region, a second end region and a middle region of the lead.

Figure 16A:
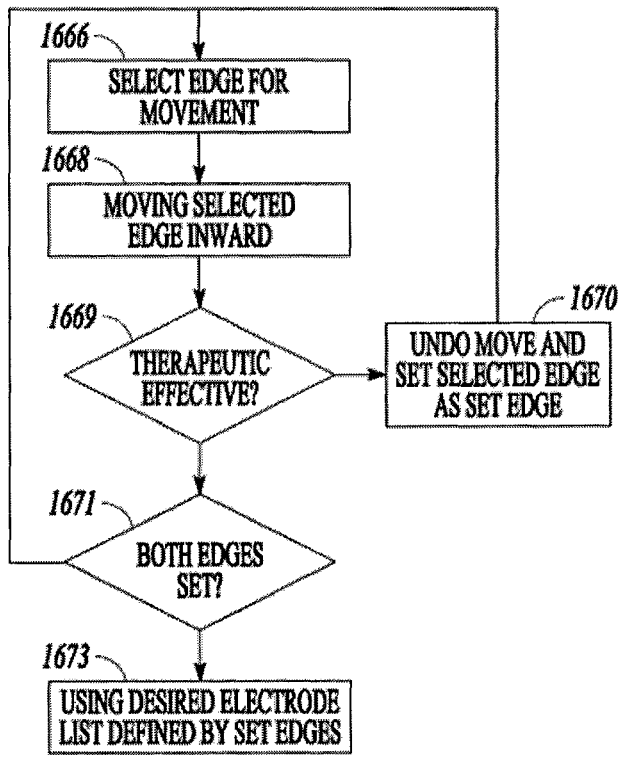
FIGS. 16A-16C illustrate, by way of example, an edge search routine.
Figure 16B:
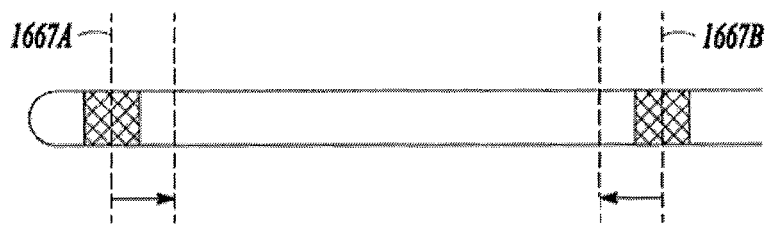
Figure 16C:
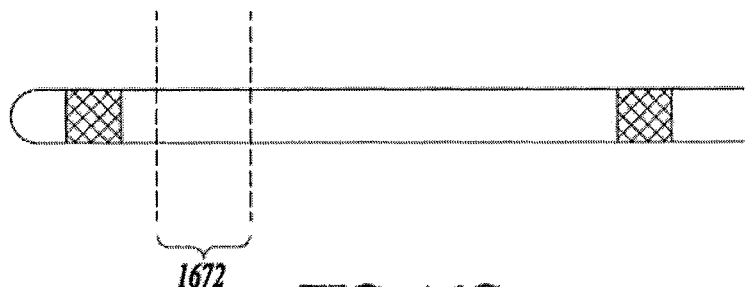

FIGS. 16A-16C illustrate, by way of example, an edge search routine. The edge search routine progressively moves each edge of the active electrodes in the array toward the middle and confirms that the neuromodulation remains effective with the moves. Thus, a first edge can be moved toward the center until the next move toward the center causes the neuromodulation to be ineffective; and a second edge can be moved toward the center until the next move toward the center causes the neuromodulation to be ineffective.

For example, the edge search routine may include selecting an edge of the electrode arrangement (e.g. array) for movement 1666. The selected edge may be one of the two edges 1667A or 1667B illustrated in FIG. 16B. However, there can be more than two edges if more than two regions are being focused. The selected edge is moved inward 1668 toward the other edge for the region of interest. If the reduced set of electrodes is no longer therapeutically effective 1669, then the previous move can be undone and that edge can be set so that is no longer is capable of being selected for movement 1670. The process can return to 1666 to attempt to move the other edge(s). If the reduced set of electrodes continues to be therapeutically effective 1669, then the process returns to 1666 to continue moving edges until such time as all of the edges are set 1671. The final reduced set 1672 of electrodes can be used 1673 to deliver the neuromodulation energy.

According to various embodiments, the programmed system may be configured with a neuromodulation focus routine such as a rostra-caudal focus routine to allow a user to select the desired electrodes for the neuromodulation to be more specific to the desired physiological area. Some embodiments may allow non-contiguous spans to be selected as a result of initial programming and/or neuromodulation refinement later on.

The neuromodulation field may be moved from location to location using an automatic trolling process or through patient control. Candidate trolling algorithms include a monopolar troll (anodic or cathodic) or a bipolar troll or a multipolar troll. The troll can be done with MICC or multiple independent voltage control, or with a timing channel interleaving technique. MICC enables the locus of the neuromodulation to be gradually moved across along the lead or within the array of electrodes. The interleaving of timing channels allows different electrode(s) in different timing channels. Values of stimulation parameter(s) (e.g. amplitude) in the timing channels can be adjusted. Thus by way of example and not limitation, if a monopolar neuromodulation is delivered using a first electrode in a first channel and another monopolar neuromodulation is delivered using a second electrode adjacent to the first electrode in a second channel, then the amplitude of the monopolar neuromodulation in the first channel may be incrementally reduced as the amplitude of the monopolar neuromodulation may be increase in the second channel. In this matter, the locus of the neuromodulation may be gradually adjusted.

Various embodiments troll a neuromodulation field, using an arrangement of electrodes on at least one lead, through neural tissue positions, and perform a quantification procedure multiple times as the neuromodulation field is trolled through the positions. The quantification procedure identifies when the neuromodulation field provides a therapeutic effect (e.g. pain relief). The quantification procedure may include receiving a marking signal that indicates that a neuromodulation intensity achieved the therapeutic effect, and storing a value for the therapeutic effect as well as neuromodulation field parameter data. The neuromodulation intensity may include neuromodulation parameters that affect the patient's perception of the neuromodulation energy. These parameters may include pulse width, rate, amplitude, distribution of current, and electrode polarity (cathode v. anode). By way of example and not limitation, the storage of the parameter data may be in a temporary storage such as but not limited to cache or RAM or in permanent/persistent storage such as but not limited to ROM, a memory device such a hard drive, optical disc, thumb drive, or cloud storage. The quantification process may include receiving a titration signal that indicates an instruction to adjust neuromodulation intensity, and adjusting the neuromodulation intensity in response to receiving the titration signal. The titration signal may be initiated by a patient, or by a clinician or other user who is responding to patient responses.

Figure 17:
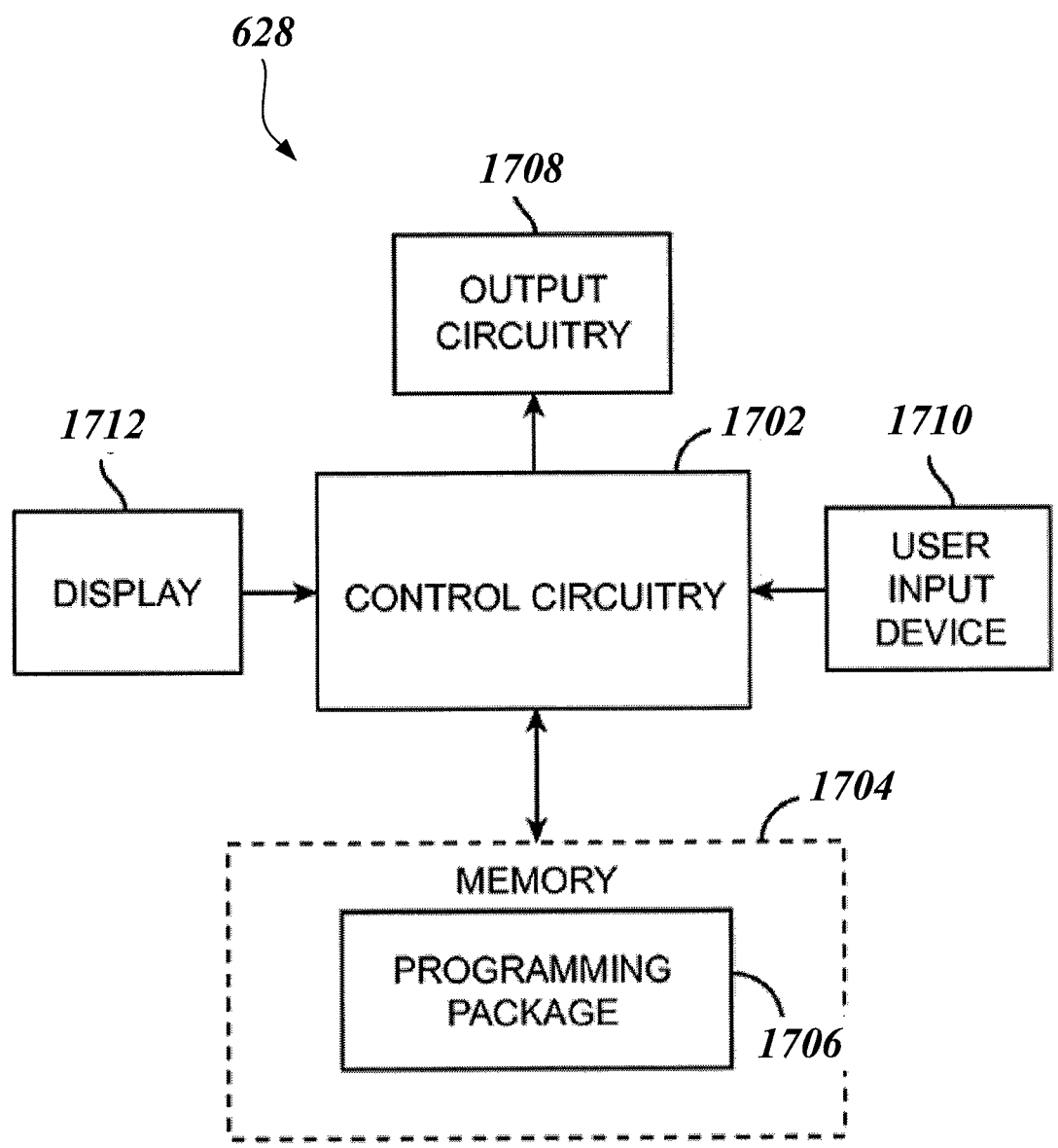
FIG. 17 is a diagram illustrating a programming device in greater detail according to an embodiment.

FIG. 17, is a diagram illustrating the CP 628 (FIG. 6) in greater detail. CP 628 includes a control circuitry 1702 (e.g., a central processor unit (CPU)) and memory 1704 that stores a stimulation programming package 1706, which can be executed by the control circuitry 1702 to allow the user to program the IPG 626 (FIG. 6), and RC 627 (FIG. 6). The CP 628 further includes output circuitry 1708 (e.g., via the telemetry circuitry of the RC 627) for downloading stimulation parameters to the IPG 626 and RC 627 and for uploading stimulation parameters already stored in the memory of the RC 627, via the telemetry circuitry of the RC 627.

Execution of the programming package 1706 by the control circuitry 1702 provides a multitude of display screens shown on display 1712 that can be navigated through via use of user input device 1710. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads, and select and program the IPG 626 with stimulation parameters in both a surgical setting and a clinical setting.

In various embodiments, execution of the programming package 1706 provides a user interface that conveniently allows a user to program the IPG 626 to produce a user-customized stimulation field, which may include the placement and movement of customized target poles. In various examples, the programming package 1706, when executed by control circuitry 1702, implements a set of engines for facilitating the user interface in which fields or target poles may be defined, mapping the field or target pole definitions to physical electrodes and electrical energy application parameters for establishing the defined fields and target poles, supervising the establishment and variation of the fields and target poles to comply with safety and other defined constraints, and optimizing the energy utilization in the operation of the IPG 626.

In the examples described above, and in various other embodiments, the components described herein are implemented as engines, circuits, components, modules, or other structures, which for the sake of consistency are termed engines, although it will be understood that these terms may be used interchangeably. Engines may be hardware, software, or firmware communicatively coupled to one or more processors in order to carry out the operations described herein. Engines may be hardware engines, and as such engines may be considered tangible entities capable of performing specified operations and may be configured or arranged in a certain manner. In an example, circuits may be arranged (e.g., internally or with respect to external entities such as other circuits) in a specified manner as an engine. In an example, the whole or part of one or more hardware processors may be configured by firmware or software (e.g., instructions, an application portion, or an application) as an engine that operates to perform specified operations. In an example, the software may reside on a machine-readable medium. In an example, the software, when executed by the underlying hardware of the engine, causes the hardware to perform the specified operations. Accordingly, the term hardware engine is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein.

Considering examples in which engines are temporarily configured, each of the engines need not be instantiated at any one moment in time. For example, where the engines comprise a general-purpose hardware processor core configured using software; the general-purpose hardware processor core may be configured as respective different engines at different times. Software may accordingly configure a hardware processor core, for example, to constitute a particular engine at one instance of time and to constitute a different engine at a different instance of time.

One aspect of the embodiments is directed to the application of customized electrotherapy fields to be applied by an IPG such as neuromodulation device 212 (FIG. 2) or IPG 626 (FIG. 6). According to some embodiments, which are described in greater detail below, a neuromodulation system such as system 210 (FIG. 2) or the SCS system of FIG. 6, facilitates the creation of customized electrotherapy fields by clinicians, physicians, or other users of the system. Customized fields in the present context include neuromodulation fields that have custom-defined size, shape, intensity, and steering parameters.

In a related embodiment, the definition of a customized field, which may be created by a user via a GUI such as GUI 214 or GUI 414, is not constrained by spatial characteristics of the physical electrodes, or of predefined virtual poles, such as target bi-poles, or tri-poles. Rather, in this type of embodiment, the GUI facilitates an arbitrary field definition. To this end, various GUI-based custom-field definition entry paradigms are provided according to various embodiments.

Figure 18A:
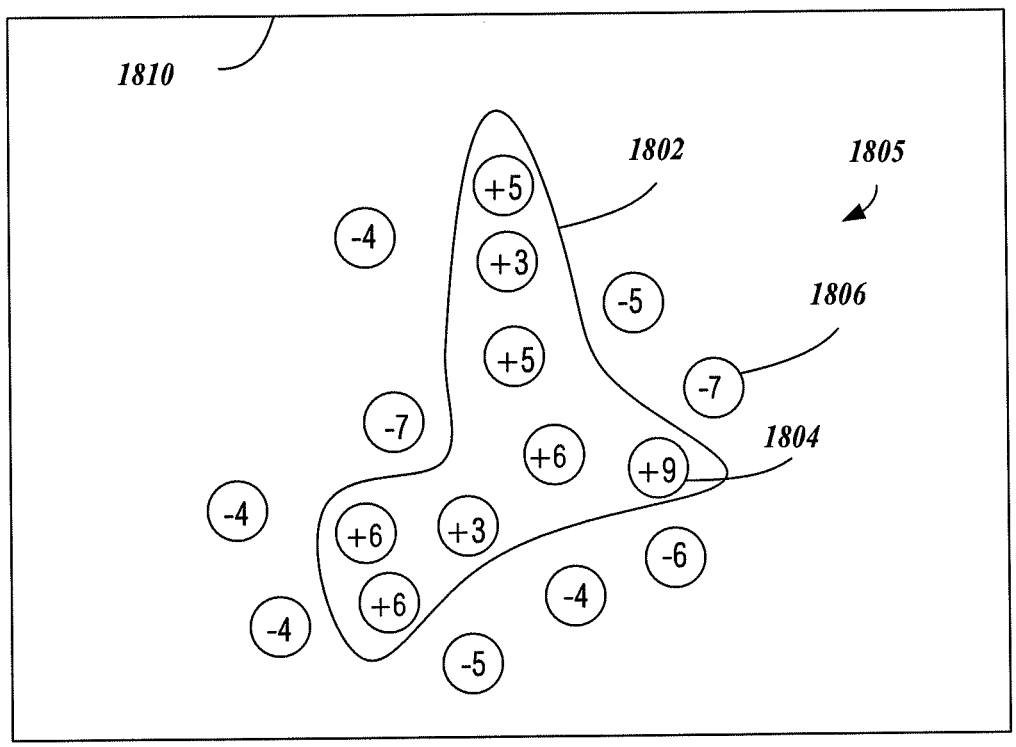
FIGS. 18A-18B are diagrams illustrating an example customized field, which may be defined according to various GUI-based embodiments.
Figure 18B:
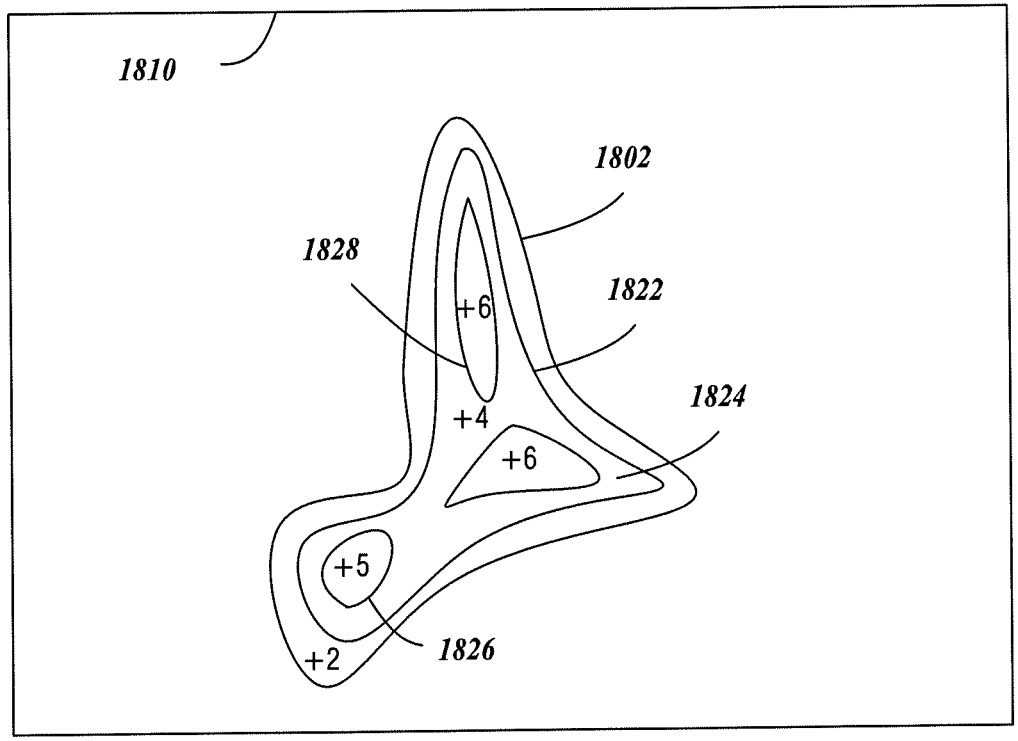

FIGS. 18A-18B are diagrams illustrating an example customized field 1802, which may be defined according to various GUI-based embodiments. In FIG. 18A, field 1802 is defined by a plurality of virtual poles 1805, including virtual anodes 1804, and virtual cathodes 1806. In one type of embodiment, a GUI 214, 414 of programming device 213, 413, 628 facilitates user-placement of virtual poles 1805 in electrotherapy target zone 1810. As illustrated, each virtual pole 1805 may have an intensity value and polarity assigned by the user. Various user-interface tools may be provided by the GUI such as, without limitation, drag-and-drop, click-and-type, increment/decrement, graphical knob, slider, and the like, to facilitate placement, and value setting, of virtual poles 1805.

In a related embodiment, the GUI displays an image representing field 1802 in target zone 1810, such as an outline, or a set of gradients, which may be color coded, based on a computation of the field 1802 in response to the locations and intensities of virtual poles 1805.

FIG. 18B is a diagram illustrating another graphical representation of customized field 1802 within electrotherapy target zone 1810, as defined by a plurality of contours. Customized field 1802 is represented by a plurality of contours 1822-1830, having various intensities, with the more centrally-located contours 1828 and 1830, and 1826 having a relatively higher intensity than the contours extending to the periphery of customized field 1802. In a related embodiment, the contours may be color coded to present a heat-map representation of the field intensity. In one type of embodiment, the GUI facilitates defining customized field 1802 by drawing the contours and assigning intensity values. The contours may be drawn via the GUI using interconnected line segments, for instance, which may be straight or curved. The field intensity of each contour may be specified numerically, as depicted, or using a visual representation such as color, shading pattern, or the like.

Figure 19:
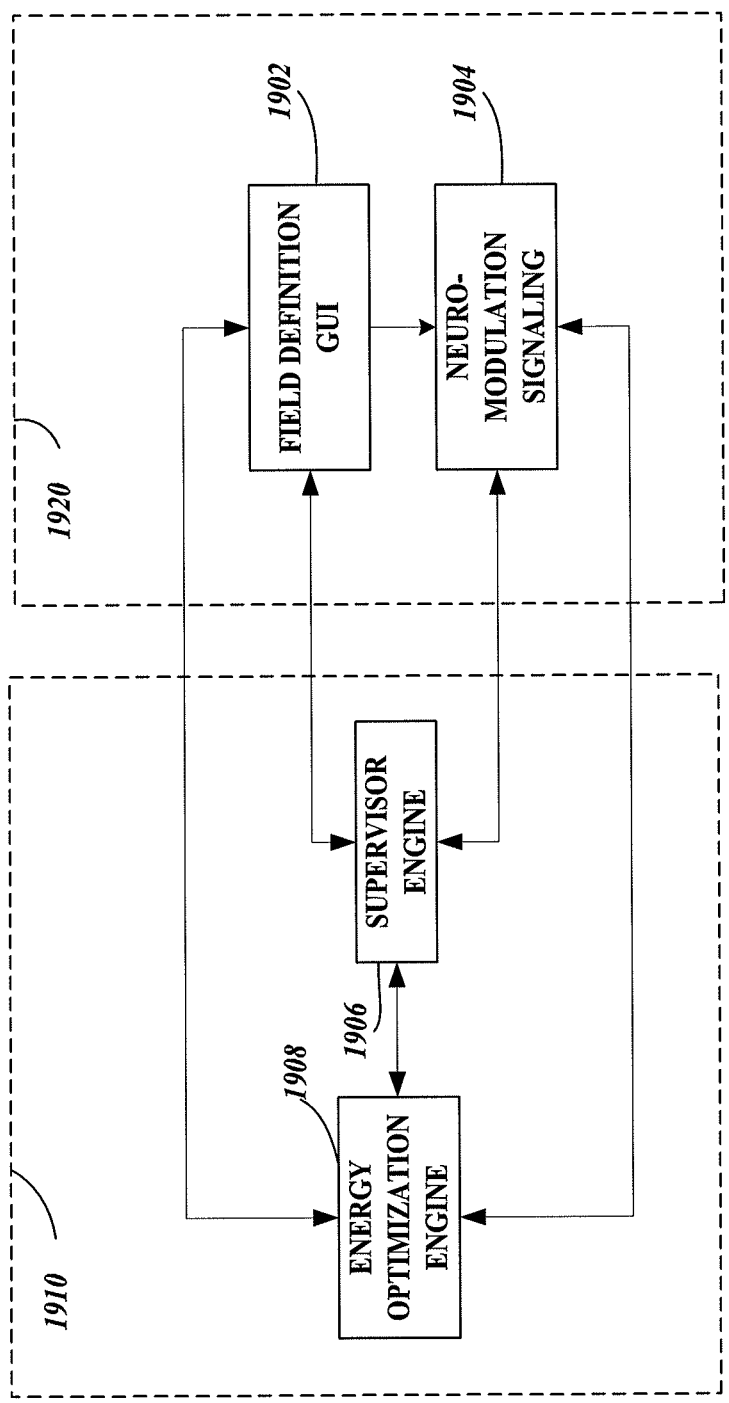
FIG. 19 is a block diagram illustrating components of a system facilitating electrotherapy field customization according to various embodiments.

FIG. 19 is a block diagram illustrating components of a system facilitating electrotherapy field customization according to various embodiments. In one type of embodiment, the system includes field definition GUI 1902 that is constructed, programmed, or otherwise configured, to facilitate and accept user input to define a customized electrotherapy field, including size, shape, and field intensity, as well as scaling and steering of the field. Field definition GUI 1902 is described in greater detail below with reference to FIG. 20.

Neuromodulation signaling engine 1904 is constructed, programmed, or otherwise configured, to generate commands for neuromodulation output circuitry, such as modulation output circuit 315 (FIG. 3) based on the custom-defined electrotherapy field 2030, that cause the neuromodulation output circuitry to generate a customized electrotherapy field in accordance with the definition. To this end, neuromodulation signaling engine 1904 may determine electrical parameters, including polarity, and fractional power, to be applied to individual physical electrodes, such as electrodes 211 (FIG. 2), 625 (FIG. 6), E1-E16 (FIG. 7), 1044 (FIG. 10), in order to generate the custom-defined electrotherapy field. Neuromodulation signaling engine 1904 is described in greater detail below with reference to FIG. 21.

Supervisor engine 1906 is constructed, programmed, or otherwise configured, to assess the electrotherapy field's compliance with applicable criteria, and based on the assessment, to control, limit, or otherwise adjust the generation of the electrotherapy field. The applicable criteria may relate to meeting patient comfort and safety needs, to meeting other specified restrictions, or to maintaining consistency of the customized electrotherapy field as it may be steered, resized, reshaped, etc. Supervisor engine 1906 is described in greater detail below with reference to FIG. 22.

Energy optimization engine 1908 is constructed, programmed, or otherwise configured, to modify the customized electrotherapy field within a permissible range in order to achieve energy savings, particularly for implanted neuromodulation devices. Energy optimization engine 1908 is described in greater detail below with reference to FIG. 23.

In various embodiments, the electrotherapy-field customization system of FIG. 19 may be implemented in a programming device such as device 213, 413, 628, for instance, or in a distributed arrangement with some components implemented in a programming device, and others in a neuromodulation device such as neuromodulation device 212 or IPG 626, for example. In the example embodiment of FIG. 19, neuromodulation device 1910 implements supervisor engine 1906 and energy optimization engine 1908, whereas programmer device 1920 implements field definition GUI 1902 and neuromodulation signaling engine 1904. It will be understood that in various other embodiments, the functionality of engines 1902-1908 may be allocated differently between programmer device 1920 and neuromodulation device 1910.

In a related embodiment, supervisor engine 1906 and energy optimization engine 1908, or portions thereof, may be duplicated in neuromodulation device 1910, and programmer device 1920. Accordingly, the supervisory and energy-optimization operations may be carried out during initial programming by the programmer device 1920 and, subsequently, in response to any modification of the custom-defined electrotherapy field (e.g., via another programmer device or via a remote control device such as RC 627 (FIG. 6), the supervisory and energy-optimization operations are carried out by neuromodulation device 1910.

Figure 20:
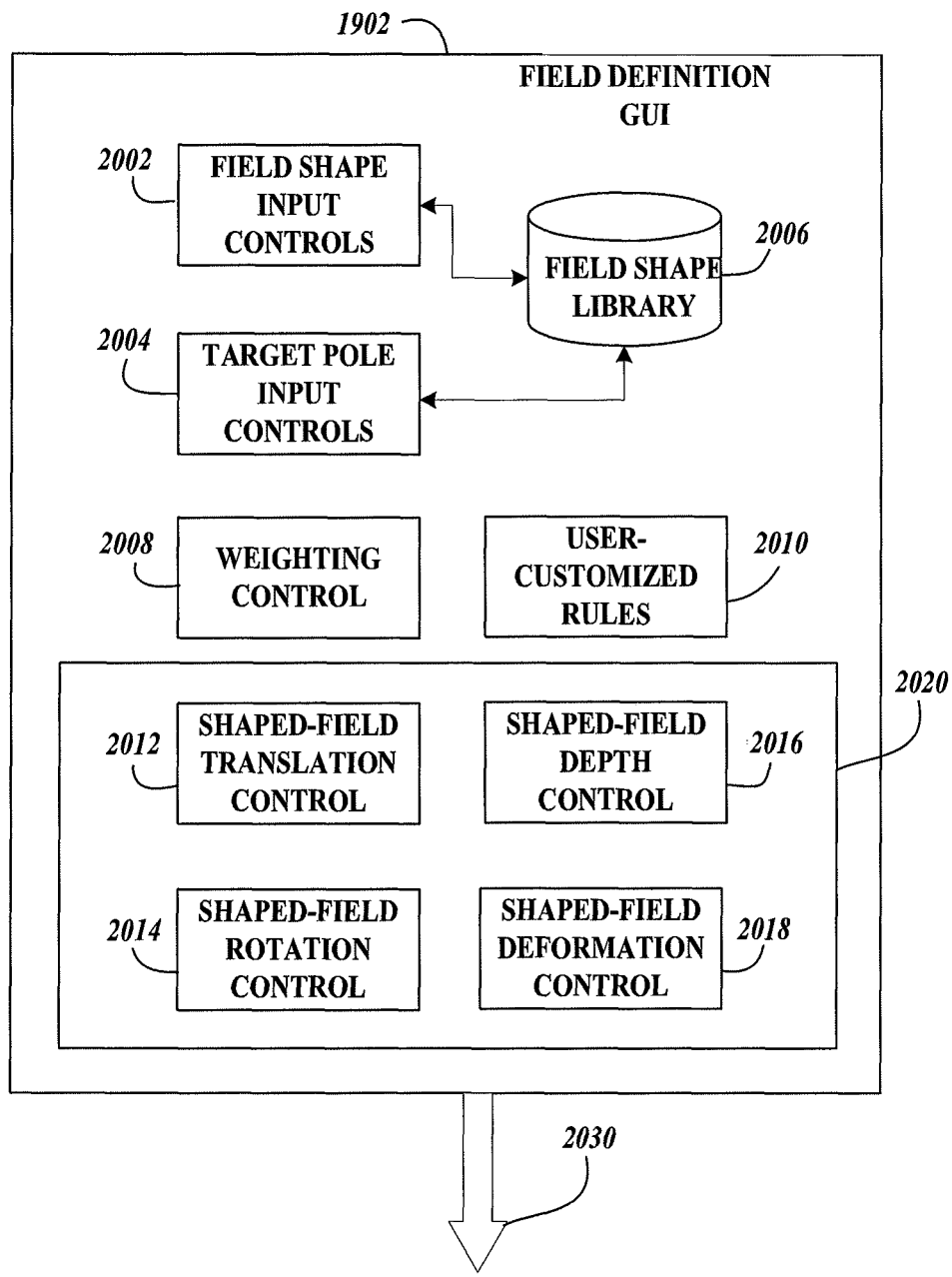
FIG. 20 is a diagram illustrating the structure and operation of a field definition GUI according to an example embodiment.

FIG. 20 is a diagram illustrating the structure and operation of field definition GUI 1902 according to an embodiment. Field shape input controls 2002 include graphical interactive objects, such as contour-drawing tools, curve fitting functions, drag-and-drop tools, point-and-click tools, virtual sliders, buttons, knobs, numeral or text entry fields, and other such interactive controls (hereinafter, user-input tools), that facilitate the defining of one or more customized electrotherapy fields by the placement or drawing of one or more contours or boundaries with corresponding polarity and intensity settings. Target pole input controls 2004 include similar user-input tools that facilitate the placement of virtual electrodes, and setting the polarity and intensity thereof. In a related embodiment, field shape input controls 2002 and target pole input controls 2004 may be used together to define an electrotherapy field.

Field shape library 2006 is a database and set of user controls that contains predefined electrotherapy field definitions, which may be browsed, selected, and modified using the user controls. Moreover, user-defined electrotherapy fields that have been created from scratch by a user, or from modification of a predefined electrotherapy field template, may be stored and organized in field shape library 2006 for use in the future.

Weighting control 2008 includes user-input tools that facilitate setting and adjusting relative intensity of various portions of the customized electrotherapy field. In various embodiments, weighting control 2008 may be in addition to, or in place of, the polarity and intensity settings that may be provided as part of field shape input controls 2002, or target pole input controls 2004. For example, supplemental field-intensity setting tools may be provided, such as highlighting, region-selection, and other user-input tools, along with corresponding intensity-setting controls.

In a related embodiment, contrary to the intensity controls that may be provided as part of field shape input controls 2002, or target pole input controls 2004, weighting control 2008 takes into account the location, size, and shape of physical electrodes relative to electrotherapy target zone 1810 in which the electrotherapy field is custom-defined. This feature facilitates more precise adjustment of portions of the field strength, such as those in very close proximity to the physical electrodes. Thus, local regions of much higher field intensity may be available in spots corresponding to physical electrodes.

In another related embodiment, weighting control 2008 is configured to scale or normalize the relative field intensity settings to the highest entered value. For instance, assuming integers are typed in as the intensity setting for various portions of the customized electrotherapy field, the highest-value integer is automatically scaled as a nominal, or reference, value, with all lower values being proportioned as a ratio relative to the nominal value. Moreover, the nominal value may be adjusted in intensity using an additional control input, such that the overall field intensity may be strengthened or weakened while maintaining the general shape of the user-defined customized electrotherapy field.

User-customized rules 2010 represent custom-specified specifications or constraints on the establishment, modification, or steering, of the customized electrotherapy field. For example, one type of user-customized rule may be an exclusion zone, or a reduced-field-intensity zone, in which a maximum limit of field intensity may be specified. The exclusion zone may be used to reduce patient discomfort if certain patient-specific sensitivity is found, while providing effective neurostimulation with high-intensity field strength in target areas.

Another type of user-customized rule may be field-steering limits, such as a boundary that defines a region where the customized electrotherapy field may be moved about. Similarly, another user-customized rule may include limits on reshaping/resizing/rotating the customized field that may be performed in the field via remote control, for example.

In some embodiments, field definition GUI 1902 includes field-steering behavior controls 2020 that allow a user to define the permissible extent of steering of the customized electrotherapy field. Field-steering behavior controls 2020 may include user-input tools such as shaped-field translation control 2012, rotation control 2014, depth control 2016, or deformation control 2018. Shaped-field translation control 2012 facilitates specifying movement of the customized electrotherapy field in rostro-cadual (up/down) and medio lateral directions, while maintaining the field's size, shape, and intensity.

Shaped-field rotation control 2014 similarly facilitates user control of rotating the customized electrostimulation field about an axis as part of the field steering. The axis may be in the center of the electrotherapy target zone, or it may be user-specified via user-input tools of the shaped-field rotation control. In various embodiments, the rotation axis may be at a fixed angle (e.g., perpendicular) to the defined customized electrotherapy field, or it may be at a user-specified angle, thereby facilitating three-dimensional rotation of the electrotherapy field, in scenarios where 3-dimensional fields are supported (e.g., where the physical electrodes are at least partially wrapped around target tissue).

Shaped-field depth control 2016 provides user-input tools for targeting the customized electrotherapy field to a specified tissue depth as part of the field steering Shaped-field deformation control 2018 provides user-input tools that facilitate specifying varying the shape of the customized electrotherapy field as part of the field steering, such as stretching or shrinking the field along one or more axes (or arcs), as may be specified by the user via the user-input tools.

In a related embodiment, shaped-field deformation control 2018 provides user-input tools that facilitate specifying varying patterns or sequences in which the shape, size, location, motion, and intensity of the electrotherapy field may be programmed. In a related example, the electrotherapy field may be programmed to change in a random or random-like sequence, with variation in the aforementioned parameters being automatically applied in response to a randomization setting. Accordingly, electrotherapy fields may be randomly or quasi-randomly selected from among a set of predefined fields, or the field-definition parameters may be randomly or quasi-randomly varied based on pre-defined variable-parameter ranges, as a function of time.

The result of the operation of these components of field definition GUI 1902 is generation of the customized field definition 2030. In various embodiments, customized field definition 2030 comprises one or more data structures that defines the dimensions and field intensities of the customized electrotherapy fields, along with any non-modifiable characteristics, constraints (such as field exclusion zones), and field-steering parameters (such as a field-steering program, along with types of permissible field steering (e.g., translation, rotation, etc.), and ranges (including limits), of configured field steering operations).

Figure 21:
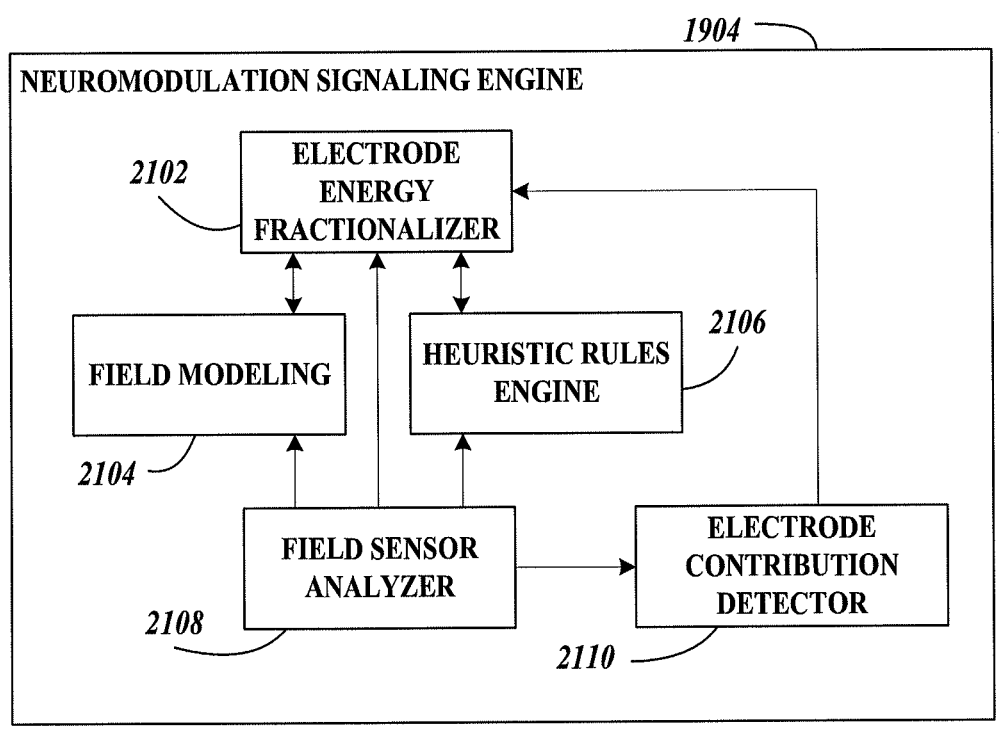
FIG. 21 is a diagram illustrating the structure and operation of neuromodulation signaling engine according to an example embodiment.

FIG. 21 is a diagram illustrating the structure and operation of neuromodulation signaling engine 1904 according to an example embodiment. At the heart of neuromodulation signaling engine 1904 is electrode energy fractionalizer 2102, which is configured to access customized field definition 2030 and, based thereupon, to generate control signaling for individually regulating the current to each physical electrode such that, collectively, the set of physical electrodes produces the customized electrotherapy field. To this end, any suitable mapping or evaluative algorithm may be applied. For example, in some embodiments, automated analytical or numerical modeling may be utilized to estimate field potential values per unit current at each of the physical electrodes at various modeled spatial observation points, such as the methodology described in detail in U.S. Pat. No. 8,412,345, the disclosure of which is incorporated by reference herein. In another type of embodiment, a set of heuristic rules for energizing the physical electrodes to achieve certain electrotherapy field characteristics, may be utilized.

In a related embodiment, a combination of algorithms may be employed. For instance, as illustrated in FIG. 21, electrode energy fractionalizer 2102 may call field modeling computational engine 2104, heuristic rules engine 2106, or some combination of these facilities. In one example, heuristic rules engine 2106 may be preconfigured with a set of rules for generating various field geometries with different corresponding electrode energization arrangements, including the use of anodes in spatial relationship with cathodes to generate and focus electric fields into certain directions or shapes. The user-entered customized electrotherapy field may be represented as a superposition of a combination of electric field forms, from which various combinations of physical electrode energizations may be selected. This initial heuristic approach carried out by heuristic rules engine 216 may be refined by analytic modeling of electric fields, performed by field modeling engine 2104, which may lead to adjustments in energization of the physical electrodes, as needed, to physically realize the customized electrotherapy field definition.

In a related embodiment, neuromodulation signaling engine 1904 further includes field sensor analyzer 2108, which is configured to receive signaling from measured portions of the actual applied field. Field measurements may be taken using certain electrodes that may be temporarily coupled to measurement circuitry. In one embodiment, field sensor analyzer 2108 is configured to compare modeled field values at locations of the measuring electrodes, to the actual measured values as measured at the measuring electrodes.

According to an example embodiment, in response to the comparison, electrode energy fractionalizer 2102 may adjust the current at one or more of the electrodes to more closely align the measured field values with those of the desired customized electrotherapy field. In addition, the field modeling engine 2104 or heuristic modeling engine 2106 may revise their machine learning algorithms to more accurately model or represent the modeled field characteristics with the actual measured field characteristics.

In another related embodiment, neuromodulation signaling engine 1904 further includes electrode contribution detector 2110, which is configured to measure the effectiveness of individual electrodes in producing the customized electrotherapy field. For instance, the measured impedance of a given electrode to one or more reference nodes may be outside of a predefined "normal" range, the occurrence of which is indicative of a potential irregularity in the electrode wiring or other circuitry, an irregularity in the implantation site, or some other malfunction. In an example, if the electrode impedance is out of the normal range, a correction factor may be added or subtracted to the current being driven to that electrode by electrode energy fractionalizer 2102 so that the contribution of the out-of-range electrode to the customized electrotherapy field falls within the expected range.

Figure 22:
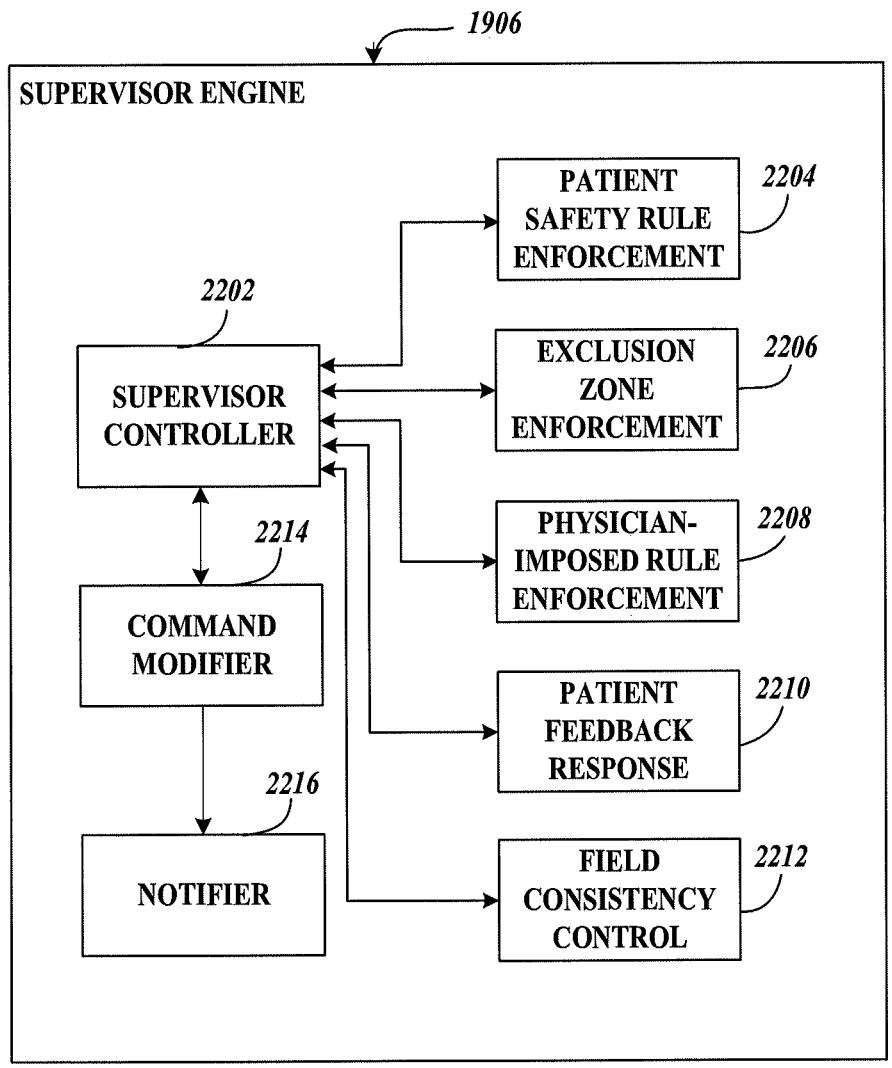
FIG. 22 is a diagram illustrating the structure and functionality of a supervisor engine according to an embodiment.

FIG. 22 is a diagram illustrating the structure and functionality of supervisor engine 1906 according to an embodiment. As discussed above, supervisor engine 1906 may be realized as part of neuromodulation device 1910, or programmer device 1920. In related embodiments, certain functions of supervisor engine 1906 may be distributed in various ways between neuromodulation device 1910 and programmer device 1920. For instance, processing of decisions based on application of heuristic rules, which tends to be less computationally intensive than matrix-inversion computations associated with modeling techniques, for example, may be carried out by the processing circuitry of neuromodulation device 1910; whereas the more computationally-intensive tasks may be carried out by the computation circuitry of programmer device 1920, according to various embodiments.

Supervisor controller engine 2202 is configured to access electrotherapy-administration commands, including those to establish customized electrotherapy fields, before the commands are carried out by neuromodulation circuitry such as modulation output circuit 315 (FIG. 3) or output circuitry 1705 (FIG. 17). In one type of embodiment, the accessed commands are commands generated by electrode energy fractionalizer 2102, which include commands that call for generation of electrical current at individual physical electrodes. In a related type of embodiment, the accessed commands include more abstracted commands based on customized field definition 2030 such as, for example, a customized electrotherapy field to be applied in response to translation, rotation, resizing, or other steering operation. Another type of command that may be accessed by supervisor controller engine 2202 is a steering input command that may not be part of customized electrotherapy field definition 2030, but input via a remote controller such as RC 627.

Supervisor controller engine 2202 calls various assessment engines to verify that the customized electrotherapy field to be produced meets safety and performance constraints. In the example depicted, the assessment engines include patient safety rule enforcement engine 2204, exclusion zone enforcement engine 2206, physician imposed rule enforcement engine 2208, patient feedback response engine 2210, and field consistency control engine 2212.

Patient safety rule enforcement engine 2204 stores various predefined constraints on electrotherapy energy application, such as current density limits, for example, which ensure patient safety and comfort. In a related embodiment, patient safety rule enforcement engine includes limits on the rate of change of electrotherapy field intensity, or rate of change of electrical current applied through each electrode. This type of rule ensures that the patient is not subjected to sudden step changes of administered neuromodulation, which might otherwise cause pain or discomfort. Patient safety rule enforcement engine 2204 assesses the electrotherapy-application commands against the predefined constraints, and reports the result of the assessment to supervisor controller 2202.

Exclusion zone enforcement engine 2206 is configured to read the customized electrotherapy field definition 2030 and extract any user-supplied limits and exclusions for the customized electrotherapy field, such as defined exclusion zones, boundaries, or the like. Exclusion zone enforcement engine 2206 reads the electrotherapy-application commands, and assesses each command against the applicable limits or field-exclusion zones. The assessment result is reported to supervisor controller 2202.

Physician-imposed rule enforcement engine 2208 maintains specific rules or constraints that may have been established by the neuromodulation therapy-prescribing physician. These physician-imposed rules may be similar by their nature to user-customized rules 2010 (FIG. 20), except that the physician-imposed rules are not specific to any particular user-customized electrotherapy field and in fact supersede any user-customized field parameters if there are any conflicts therebetween. Similar in operation to exclusion zone enforcement engine 2206, physician-imposed rule enforcement engine 2208 assesses each command for compliance with the applicable physician-imposed rules, and reports the assessment result to supervisor controller 2202.

Patient feedback response engine 2210 is configured to read an input that represents a response of the patient to the applied electrotherapy. The input may be obtained via a programming device (e.g., 213, 413) or remote controller RC 627 according to some examples. In other examples, the neuromodulation device 212 or IPG 626 may include motion or auditory sensing and associated digitizing and processing circuitry to detect indicia of patient discomfort, and the result of such detection may constitute the input to patient feedback response engine 2210. Patient feedback response engine 2210 reports any assessment of patient discomfort to supervisor controller engine 2202.

Field consistency control engine 2212 is configured to read the customized electrotherapy field definition 2030 and the electrotherapy-application commands, and to assess whether execution of each given command would cause the resulting electrotherapy field to violate the customized field definition 2030. Accordingly, the field consistency control engine operates to preserve the integrity of the customized electrotherapy field during steering of the customized electrotherapy field. A set of preconfigured variation tolerance limits, such as +/−5% for field intensity variation or +/−10% for field boundary variation, for example, may be applied. Accordingly, any command that calls for steering of the customized electrotherapy field is checked for its effect on the integrity of the field, within the permissible steering-related parameters in the customized electrotherapy field definition 2030, and within any variation tolerance limits. The result of any would-be field-definition violation is reported to supervisor controller 2202.

In response to the reported results from one or more of the assessment engines 2204-2212, supervisor controller 2202 may either permit execution of the command, or it may pass the reported exception report(s) to command modifier 2214. Command modifier 2214 is configured to modify the command in response to a reported exception by supervisor controller 2202. Command modification may involve varying the control of the electrotherapy field to adjust the called-for field intensity distribution, positioning, rate of change for one or more field parameters, or the like, in order to resolve the assessed exception.

In one embodiment, command modifier 2214 modifies the customized electrotherapy field definition 2030 to resolve the assessed exception. In a related embodiment, command modifier 2214 operates at the level of electrotherapy signaling generation commands that are produced by neuromodulation signaling engine 1904.

In a related embodiment, command modifier 2214 is configured with a set of heuristic rules for adjusting various attributes of the electrotherapy field, such as size, shape, intensity, uniformity, steering, and the like, in a computationally-efficient manner than may be executed on a programming device or on a processing circuit of the neuromodulation device in some embodiments. In a related embodiment, command modifier engine 2214 is configured to work iteratively with supervisor controller, and in turn, with assessment engines 2204-2212, such that modified commands may be verified to be compliant with applicable rules.

Notifier engine 2216 is configured to report any command modification and any inability of command modifier 2214 to produce the customized electrotherapy field that meets the electrotherapy field definition 2030 within permitted tolerance, to a programming device or remote controller through which the user may be informed.

Figure 23:
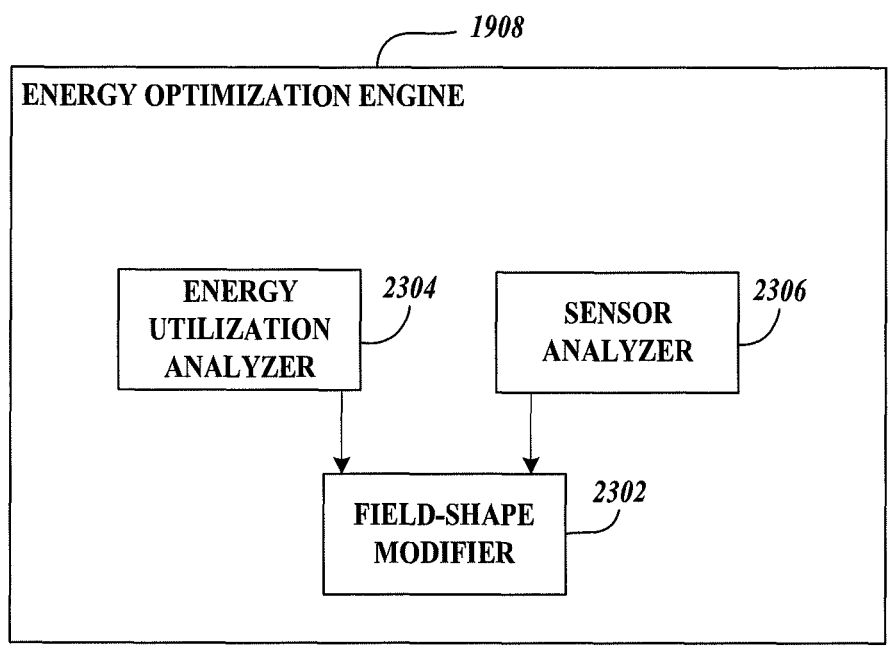
FIG. 23 is a diagram illustrating the structure and functionality of an energy optimization engine according to an embodiment.

FIG. 23 is a diagram illustrating the structure and functionality of energy optimization engine 1908 according to an embodiment. As discussed above with reference to supervisor engine 1906, energy optimization engine 1908 may be realized in neuromodulation device 1910, programmer device 1920, or by a combination of these devices, according to various embodiments. Energy optimization engine 1908 includes field-shape modifier engine 2302, which is configured to make adjustments to the customized electrotherapy field in order to improve efficiency of energy utilization. As an example use case, a customized electrotherapy field definition may call for a field shape that may be most effectively produced with the use of closely-spaced anodes and cathodes. However, close spacing of opposing-polarity electrodes may result in high energy consumption with minimal contribution to the therapeutic field. Accordingly, in an embodiment, energy utilization analyzer reads electrotherapy field definition 2030, as well as associated commands, and determines if the custom-defined electrotherapy field, or the control signaling to the physical electrodes to establish the customized electrotherapy field, tends to present any inefficiencies.

In some embodiments, sensor analyzer engine 2306 is configured to read measurements made by one or more sensors, such as current measurement circuits that may be switchably connected with electrode-driving circuitry to measure the applied current to individual electrodes, or groups of electrodes according to various embodiments. Actual current readings may be indicative of poor energy efficiency.

Based on the output of energy utilization analyzer 2304 and sensor analyzer 2306, field-shape modifier 2302 operates to adjust the customized electrotherapy field to resolve the identified causes of energy inefficiency. As a result, in one embodiment, a modified electrotherapy field definition, to be used in place of custom-defined electrotherapy field definition 2030, is generated. In a related embodiment, the modified electrotherapy field may be passed to supervisor engine 1906 for evaluation as described above.

In another embodiment, field-shape modifier engine 2302 operates at the level of electrotherapy signaling generation commands that are produced by neuromodulation signaling engine 1904. Accordingly, individual fractionalized currents to one or more electrodes may be adjusted to achieve available energy savings.

In addition to the Examples discussed in the Summary Section above, some other non-limiting examples are provided as follows.

Example 26 is a method for customizing a neuromodulation field, the method comprising: providing a user interface having a set of input controls to accept a customized electrotherapy field definition, wherein the input controls include controls for defining field shape, field intensity, and field steering parameters of the customized electrotherapy field; producing commands for neuromodulation output circuitry to control generation of a customized electrotherapy field via a set of electrodes based on the customized electrotherapy field definition; assessing compliance of the customized electrotherapy field to be generated with applicable predefined criteria; and modifying generation of the customized electrotherapy field in response to an assessed non-compliance with the criteria.

In Example 27, the subject matter of Example 26 optionally includes wherein the input controls include steering-behavior controls that facilitate definition of permissible steering of the customized electrotherapy field.

In Example 28, the subject matter of any one or more of Examples 26-27 optionally include wherein producing the commands includes: accessing the customized field definition; and generating control signaling for individually regulating electrical current to individual ones of the set of electrodes such that, collectively, the set of electrodes produces the customized electrotherapy field, wherein the control signaling is determined based on a combination of electrotherapy field modeling and application of heuristic rules.

In Example 29, the subject matter of any one or more of Examples 26-28 optionally include receiving measurements of field properties of an applied electrotherapy field, the measurements having been taken at a plurality of measurement locations; and comparing modeled field values at locations corresponding to the measurement locations to the field properties as measured.

In Example 30, the subject matter of any one or more of Examples 26-29 optionally include measuring an effectiveness of individual electrodes in producing the customized electrotherapy field.

In Example 31, the subject matter of any one or more of Examples 26-30 optionally include wherein the applicable predefined criteria includes patient safety rules that are nonspecific to the customized electrotherapy field, and user-defined field-behavior rules that are specific to the customized electrotherapy field.

In Example 32, the subject matter of any one or more of Examples 26-31 optionally include wherein the applicable predefined criteria includes exclusion zone rules that define areas from which the electrotherapy field is to be excluded.

Example 33 is a neuromodulation customization system, comprising: means for carrying out the method according to any one of Examples 26-32.

In Example 34, the subject matter of Example 33 optionally includes wherein the means include: a field definition user interface to facilitate entry of a customized electrotherapy field definition, the field definition user interface including a set of input controls for defining field shape, field intensity, and field steering parameters of the customized electrotherapy field; a neuromodulation signaling engine to produce commands for neuromodulation output circuitry to control generation of a customized electrotherapy field via a set of electrodes based on the customized electrotherapy field definition; and a supervisor engine to assess compliance of the customized electrotherapy field to be generated with applicable predefined criteria, and to modify generation of the customized electrotherapy field in response to an assessed non-compliance with the criteria.

In Example 35, the subject matter of any one or more of Examples 33-34 optionally include wherein the means are implemented on a programmer device that is adapted to be communicatively coupled to a neuromodulation device that includes the neuromodulation output circuitry.

In Example 36, the subject matter of Example 35 optionally includes wherein the supervisor engine is implemented on a neuromodulation device that includes the neuromodulation output circuitry.

In Example 37, the subject matter of any one or more of Examples 34-36 optionally include, wherein the supervisor engine is implemented on both, a programmer device that is adapted to be communicatively coupled to a neuromodulation device, and on the neuromodulation device.

In Example 38, the subject matter of any one or more of Examples 34-37 optionally include, wherein the set of input controls includes graphical interactive virtual pole placement and intensity-setting controls, wherein operation of the virtual pole placement and intensity-setting controls defines the customized electrotherapy field.

In Example 39, the subject matter of any one or more of Examples 34-38 optionally include, wherein the set of input controls includes graphical interactive field contour placement and intensity-setting controls, wherein operation of the field contour placement and intensity-setting controls defines the customized electrotherapy field.

In Example 40, the subject matter of any one or more of Examples 34-39 optionally include, wherein the applicable predefined criteria includes constraints on a rate of change of electrotherapy field administration.

Example 41 is non-transitory machine-readable medium comprising instructions that, when executed on a processor-based system for customizing a neuromodulation field, cause the system to: provide a user interface having a set of input controls to accept a customized electrotherapy field definition, wherein the input controls include controls for defining field shape, field intensity, and field steering parameters of the customized electrotherapy field; produce commands for neuromodulation output circuitry to control generation of a customized electrotherapy field via a set of electrodes based on the customized electrotherapy field definition; assess compliance of the customized electrotherapy field to be generated with applicable predefined criteria; and modify generation of the customized electrotherapy field in response to an assessed non-compliance with the criteria.

The above detailed description is intended to be illustrative, and not restrictive. The scope of the disclosure should, therefore, be determined with references to the appended claims, along with the full scope of equivalents to which such claims are entitled.

What is claimed is:

1. A neuromodulation customization system for use with a neuromodulation device having neuromodulation output circuitry to generate an electrotherapy field via a set of electrodes, the neuromodulation customization system comprising:
   a field definition user interface to facilitate entry of a customized electrotherapy field definition to define at least a field shape and a field intensity for a customized electrotherapy field, the field definition user interface including a set of input controls for defining the field shape, the field intensity, and field steering parameters of the customized electrotherapy field;
   a neuromodulation signaling engine to produce commands for the neuromodulation output circuitry to control generation of the customized electrotherapy field via the set of electrodes based on the customized electrotherapy field definition; and
   a supervisor engine to assess compliance of the defined field shape and the defined field intensity for the customized electrotherapy field to be generated with applicable predefined criteria, and to control generation of the customized electrotherapy field based on assessed non-compliance with the criteria.

2. The neuromodulation customization system of claim 1, wherein:

the field definition user interface, the neuromodulation signaling engine, and the supervisor engine are implemented on a programmer device that is adapted to be communicatively coupled to the neuromodulation device that includes the neuromodulation output circuitry; or the supervisor engine is implemented on the neuromodulation device that includes the neuromodulation output circuitry; or the supervisor engine is implemented on both, a programmer device that is adapted to be communicatively coupled to the neuromodulation device, and on the neuromodulation device.

3. The neuromodulation customization system of claim 1, wherein the set of input controls includes graphical interactive virtual pole placement and intensity-setting controls, wherein operation of the virtual pole placement and intensity-setting controls defines the customized electrotherapy field.

4. The neuromodulation customization system of claim 1, wherein the set of input controls includes graphical interactive field contour placement and intensity-setting controls, wherein operation of the field contour placement and intensity-setting controls defines the customized electrotherapy field.

5. The neuromodulation customization system of claim 1, wherein the field definition interface includes a field shape library that includes previously-defined customized field definitions.

6. The neuromodulation customization system of claim 1, wherein the field definition interface includes user-customized rules that impose a set of constraints of the customized electrotherapy field.

7. The neuromodulation customization system of claim 1, wherein the field definition interface includes a set of steering-behavior controls that facilitate definition of permissible steering of the customized electrotherapy field.

8. The neuromodulation customization system of claim 7, wherein the steering-behavior controls include controls for defining translation, rotation, and deformation behavior of the customized electrotherapy field.

9. The neuromodulation customization system of claim 1, wherein the neuromodulation signaling engine includes an electrode energy fractionalizer to access the customized field definition, and to generate control signaling for individually regulating electrical current to individual ones of the set of electrodes such that, collectively, the set of electrodes produces the customized electrotherapy field, wherein the control signaling is determined based on a combination of electrotherapy field modeling and application of heuristic rules.

10. The neuromodulation customization system of claim 1, wherein the neuromodulation signaling engine includes a field sensor analyzer to receive measurements of field properties of an applied electrotherapy field, the measurements having been taken at a plurality of measurement locations, and to compare modeled field values at locations corresponding to the measurement locations to the field properties as measured.

11. The neuromodulation customization system of claim 1, wherein the neuromodulation signaling engine includes an electrode contribution detector to measure an effectiveness of individual electrodes in producing the customized electrotherapy field.

12. The neuromodulation customization system of claim 1, wherein the applicable predefined criteria includes at least one of:

patient safety rules that are nonspecific to the customized electrotherapy field, and user-defined field-behavior rules that are specific to the customized electrotherapy field;

exclusion zone rules that define areas from which the electrotherapy field is to be exclude;

physician-imposed rules that are nonspecific to the customized electrotherapy field; or constraints on a rate of change of electrotherapy field administration.

13. The neuromodulation customization system of claim 1, further comprising:

an energy optimization engine to assess whether generation of the customized electrotherapy field includes any correctable energy inefficiencies, and to modify generation of the customized electrotherapy field to resolve one or more causes of the energy inefficiencies.

14. A non-transitory machine-readable medium comprising instructions that, when executed on a processor-based system for customizing a neuromodulation field, cause the system to:

provide a user interface having a set of input controls to accept a customized electrotherapy field definition to define at least a field shape and a field intensity for a customized electrotherapy field, wherein the input controls include controls for defining the field shape, the field intensity, and field steering parameters of the customized electrotherapy field;

produce commands for neuromodulation output circuitry to control generation of the customized electrotherapy field via a set of electrodes based on the customized electrotherapy field definition;

assess compliance of the defined field shape and the defined field intensity for the customized electrotherapy field to be generated with applicable predefined criteria; and control generation of the customized electrotherapy field based on assessed non-compliance with the criteria.

15. The machine-readable medium of claim 14, wherein:

the applicable predefined criteria includes patient safety rules that are nonspecific to the customized electrotherapy field, and user-defined field-behavior rules that are specific to the customized electrotherapy field, and exclusion zone rules that define areas from which the electrotherapy field is to be excluded;

the input controls include steering-behavior controls that facilitate definition of permissible steering of the customized electrotherapy field;

the instructions to produce the commands includes instructions for:

accessing the customized field definition; and generating control signaling for individually regulating electrical current to individual ones of the set of electrodes such that, collectively, the set of electrodes produces the customized electrotherapy field, wherein the control signaling is determined based on a combination of electrotherapy field modeling and application of heuristic rules; and wherein the machine-readable medium further comprises instructions for:

receiving measurements of field properties of an applied electrotherapy field, the measurements having been taken at a plurality of measurement locations;

comparing modeled field values at locations corresponding to the measurement locations to the field properties as measured; and measuring an effectiveness of individual electrodes in producing the customized electrotherapy field.

16. A method for customizing a neuromodulation field, comprising:

providing a user interface having a set of input controls to accept a customized electrotherapy field definition to define at least a field shape and a field intensity for a customized electrotherapy field, wherein the input controls include controls for defining the field shape, the field intensity, and field steering parameters of the customized electrotherapy field;

controlling generation of the customized electrotherapy field via a set of electrodes based on the customized electrotherapy field definition;

assessing compliance of the defined field shape and the defined field intensity for the customized electrotherapy field to be generated with applicable predefined criteria; and controlling generation of the customized electrotherapy field based on assessed non-compliance with the criteria.

17. The method of claim 16, further comprising defining the customized electrotherapy field using graphical interactive virtual pole placement and intensity-setting controls.

18. The method of claim 16, further comprising defining the customized electrotherapy field using graphical interactive field contour placement and intensity-setting controls.

19. The method of claim 16, further comprising using steering-behavior controls for defining permissible steering of the customized electrotherapy field.

20. The method of claim 19, wherein using the steering-behavior controls includes using controls for defining translation, rotation, and deformation behavior of the customized electrotherapy field.

* * * * *